United States Patent [19]

Oxford et al.

[11] Patent Number: 4,994,483
[45] Date of Patent: Feb. 19, 1991

[54] 5-SUBSTITUTED-3-AMINOALKYL INDOLE DERIVATIVES FOR MIGRAINE

[75] Inventors: Alexander W. Oxford, Royston; Brian Evans, Buntingford; Michael D. Dowle, Ware; Ian H. Coates, Hertford, all of England

[73] Assignee: Glaxo Group Limited, England

[21] Appl. No.: 443,874

[22] Filed: Nov. 30, 1989

Related U.S. Application Data

[63] Continuation of Ser. No. 72,786, Jul. 13, 1987, abandoned, which is a continuation of Ser. No. 678,995, Dec. 6, 1984, abandoned.

[30] Foreign Application Priority Data

Dec. 6, 1983 [GB] United Kingdom ............. 83 32435

[51] Int. Cl.$^5$ ................ C07D 209/16; C07D 209/14; A61K 31/40
[52] U.S. Cl. ................... 514/415; 514/930; 548/504; 548/505
[58] Field of Search ............... 514/415; 548/504, 505

[56] References Cited

U.S. PATENT DOCUMENTS

| | | | |
|---|---|---|---|
| 3,322,787 | 5/1967 | Sletzinger | 548/500 |
| 3,468,882 | 9/1969 | Laskowski | 548/373 |
| 3,472,870 | 10/1969 | Larsen | 548/504 |
| 3,624,103 | 11/1971 | De Mantiis | 548/500 |
| 4,283,410 | 8/1981 | Schut | 548/500 |
| 4,636,521 | 1/1987 | Coates | 548/504 |
| 4,672,067 | 6/1987 | Coates | 548/504 |
| 4,785,016 | 11/1988 | Evans | 514/415 |
| 4,816,470 | 3/1989 | Dowle | 514/415 |
| 4,894,387 | 1/1990 | Butina | 514/415 |

OTHER PUBLICATIONS

Green, "Protective Groups in Organic Synthesis", 1981, pp. 218-220.
Handbook of Experimental Pharmacology, vol. XIX, Springer-Verlag, New York, 1966.
A Manual of Pharmacology, Sollmann, 8th Ed., pp. 45-47.
Proposals for the Classification and Nomenclature of Functional Receptors and 5-Hydroxytryptamine, Neuropharmacology, vol. 25, No. 6, pp. 563-576, 1986.
Pharmacological Principles and Practice, Paton, pp. 1-2.
The Pharmacological Basis of Therapeutics, 7th Ed., pp. 35-37.
Evidence for Two Types of Excitatory Receptor for 5-Hydroxytryptamine in Dog Isolated Vasculature, Apperley, pp. 2215-223, Re J. Pharmac (1980).

*Primary Examiner*—Mark L. Berch
*Attorney, Agent, or Firm*—Bacon & Thomas

[57] ABSTRACT

Indole derivatives are disclosed of the general formula (I):

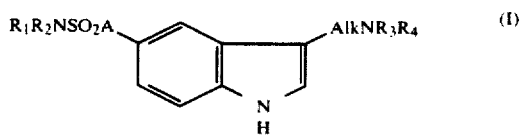

wherein $R_1$ is hydrogen, $C_{1-6}$ alkyl or $C_{3-6}$ alkenyl; $R_2$ is a hydrogen, $C_{1-3}$ alkyl, $C_{3-6}$ alkenyl, phenyl, phen($C_{1-4}$)alkyl or $C_{5-7}$ cycloalkyl; $R_3$ and $R_4$ are hydrogen, $C_{1-3}$ alkyl or propenyl groups or together form an aralkylidene group; Alk is $C_2$-$C_3$ alkylene chain and A is $C_2$-$C_5$ alkylene chain and its physiologically acceptable salts and solvates.

The compounds may be prepared, for example, by cyclization of a compound of general formula (II):

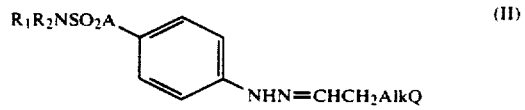

where Q is the group $NR_3R_4$ or a protected derivative thereof or a leaving group and $R_1$, $R_2$, $R_3$, $R_4$, A and Alk are as defined for formula (I).

The compounds have a selective vosoconstrictor action and are useful in treating pain such as migraine. The compounds may be formulated as pharmaceutical compositions in conventional manner, preferably for oral administration.

5 Claims, No Drawings

5-SUBSTITUTED-3-AMINOALKYL INDOLE DERIVATIVES FOR MIGRAINE

This application is a continuation of application Ser. No. 07,072,786, filed July. 13, 1987, which is a continuation of application Ser. No. 06/678,995, filed Dec. 6, 1984, both now abandoned.

This invention relates to indole derivatives, to processes for their preparation, to pharmaceutical compositions containing them and to their medical use, in particular to compounds and compositions of use in the treatment of migraine.

The pain of migraine is recognised as being primarily of vascular origin, caused by excessive dilatation of the cranial vasculature. Known treatments for migraine include the administration of compounds having vasoconstrictor properties such as ergotamine. However, ergotamine is a non-selective vasoconstrictor which constricts blood vessels throughout the body and has undesirable and potentially dangerous side effects. Migraine may also be treated by administering an analgesic usually in combination with an antiemetic but such treatments are of limited value.

There is thus a need for a safe and effective drug for the treatment of migraine, which can be used either prophylactically or to alleviate an established headache, and a compound having a selective vasoconstrictor activity would fulfil such a role.

We have now found a group of indole derivatives having potent and selective vasoconstrictor activity.

The present invention provides an indole of the general formula (I):

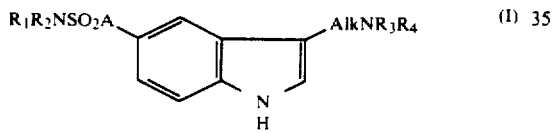

wherein
$R_1$ represents a hydrogen atom or a $C_{1-6}$ alkyl or $C_{3-6}$ alkenyl group;
$R_2$ represents a hydrogen atom or a $C_{1-3}$ alkyl, $C_{3-6}$ alkenyl, phenyl, phen($C_{1-4}$)alkyl or $C_{5-7}$ cycloalkyl group;
$R_3$ and $R_4$, which may be the same or different, each represents a hydrogen atom or a $C_{1-3}$ alkyl or 2-propenyl group or $R_3$ and $R_4$ together form an aralkylidene group; Alk represents an alkylene chain containing two or three carbon atoms which may be unsubstituted or substituted by not more than two $C_{1-3}$ alkyl groups; and
A represents an alkylene chain containing two to five carbon atoms which may be unsubstituted or substituted by not more than two $C_{1-3}$ alkyl groups,
and physiologically acceptable salts and solvates (e.g. hydrates) thereof.

The invention includes within its scope all optical isomers of compounds of general formula (I) and their mixtures including the racemic mixtures thereof.

Referring to the general formula (I), the alkyl groups in the general formula (I) may be straight chain or branched chain alkyl groups containing 1 to 3 carbon atoms, or, in the case of $R_1$, 1 to 6, preferably 1 to 3, carbon atoms. Examples of alkyl groups include methyl, ethyl, propyl and isopropyl groups. The alkenyl groups preferably contain 3 or 4 carbon atoms, examples being propenyl and butenyl groups. It will be understood that when $R_1$ or $R_2$ is an alkenyl group the double bond must be separated from the nitrogen atom by at least one methylene group. The cycloalkyl groups preferably contain 5 or 6 carbon atoms and examples include cyclopentyl and cyclohexyl groups. The alkyl moieties of the phenalkyl groups preferably contain 1 or 2 carbon atoms as in e.g. benzyl and phenethyl groups. The aralkylidene group is preferably an aryl methylidene group such as benzylidene.

In the compounds of general formula (I) it is preferred that at least one of $R_1$ and $R_2$ represents hydrogen.

A is preferably an unsubstituted alkylene chain containing two to five carbon atoms, especially two or three carbon atoms. Alk is preferably an unsubstituted alkylene chain, especially an unsubstituted alkylene chain containing two carbon atoms.

A preferred class of compounds represented by the general formula (I) is that in which $R_1$ represents a hydrogen atom or a $C_{1-6}$ alkyl group and $R_2$ represents a hydrogen atom or a $C_{1-3}$ alkyl, or phen($C_{1-4}$) alkyl group.

Another preferred class of compounds represented by the general formula (I) is that in which A represents the —CH$_2$CH$_2$—group.

A further preferred class of compounds is that wherein, in the general formula (I), $R_3$ and $R_4$, which may be the same or different, each represents a hydrogen atom or a $C_{1-3}$ alkyl group.

A preferred class of compounds falling within the scope of general formula (I) is that represented by the general formula (Ia):

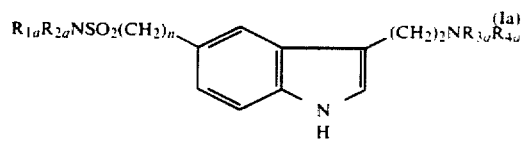

wherein
$R_{1a}$ represents a hydrogen atom or a $C_{1-3}$ alkyl group;
$R_{2a}$ represents a hydrogen atom or a $C_{1-3}$ alkyl, or phen($C_{1-2}$) alkyl group;
$R_{3a}$ and $R_{4a}$ which may be the same or different each represents a hydrogen atom or a methyl or ethyl group; and
n represents 2 or 3,
and physiologically acceptable salts and solvates (e.g. hydrates) thereof.

A particularly preferred class of compounds according to the invention is that represented by the general formula (Ib):

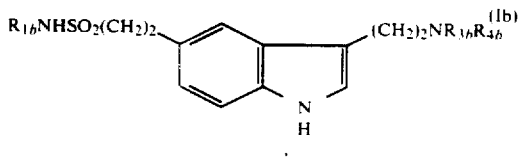

wherein
$R_{1b}$ represents a hydrogen atom or a $C_{1-3}$ alkyl group; and $R_{3b}$ and $R_{4b}$, which may be the same or different, each represents a hydrogen atom or a methyl or ethyl group;

and physiologically acceptable salts and solvates, (e.g. hydrates) thereof.

In compounds of formula (Ib) it is preferred that the total number of carbon atoms in $R_{3b}$ and $R_{4b}$ does not exceed two, and most preferably $R_{3b}$ and $R_{4b}$ each represents a methyl group.

Preferred compounds according to the invention include:

3-[2-(ethylamino)ethyl]-N-methyl]-1H-indole-5-ethanesulphonamide;

N-methyl-3-[2-(methylamino)ethyl]-1H-indole-5-ethanesulphonamide;

3-(2-aminoethyl)-N-methyl-1H-indole-5-ethanesulphonamide;

3-[2-(dimethylamino)ethyl]-1H-indole-5-ethanesulphonamide;

3-[2-(dimethylamino)ethyl]-N-methyl-1H-indole-5-ethanesulphonamide; and the physiologically acceptable salts and solvates (e.g. hydrates) of these compounds.

Suitable physiologically acceptable salts of the indole of general formula (I) include acid addition salts formed with organic or inorganic acids for example hydrochlorides, hydrobromides, sulphates, fumarates, maleates and succinates. Other salts may be useful in the preparation of the compounds of general formula (I) e.g. creatinine sulphate adducts and oxalates.

It will be appreciated that the invention extends to other physiologically acceptable equivalents of the compounds according to the invention, i.e. physiologically acceptable compounds which are converted in vivo into the parent compound. Examples of such equivalents include physiologically acceptable labile N-acyl derivatives such as the N-acetyl derivative.

Compounds of the invention selectively constrict the carotid arterial bed of the anaesthetised dog, whilst having a negligible effect on blood pressure. The selective vasoconstrictor action of compounds of the invention has been demonstrated in vitro.

Compounds of the invention are useful in treating pain resulting from dilatation of the cranial vasculature, in particular migraine and cluster headache.

In particular, the compounds of formula (Ib) previously defined have been found to be highly selective vasoconstrictors and to be extremely potent in their action. Compounds of general formula I(b) are rapidly absorbed from the gastro-intestinal tract and are suitable for oral or rectal administration. Compounds of formula (Ib) exhibit no toxic or undesirable effects in rats at doses up to 10mg/kg At doses at which the compounds of formula (Ib) would be efficaceous in the treatment of migraine, the compounds have no significant effect on blood pressure and heart rate and no significant bronchoconstrictor effect on the lung.

Accordingly the invention also provides a pharmaceutical composition adapted for use in medicine which comprises at least one compound of formula (I) or a physiologically acceptable salt or solvate (e.g. hydrate) thereof and which is formulated for administration by any convenient route. Such compositions may be formulated in conventional manner using one or more pharmaceutically acceptable carriers or excipients.

Thus the compounds according to the invention may be formulated for oral, buccal, parenteral or rectal administration or in a form suitable for administration by inhalation or insufflation. Formulations of the compounds according to the invention for oral administration are preferred.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose; fillers (e.g. lactose, microcrystalline cellulose or calcium hydrogen phosphate); lubricants (e.g. magnesium stearate, talc or silica); disintegrants (e.g. potato starch, sodium starch glycollate or croscarmellose); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives e.g. hydroxypropylmethylcellulose or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl p-hydroxybenzoates or sorbic acid). The liquid preparations may also contain conventional buffers, flavouring, colouring and sweetening agents as appropriate.

For buccal administration the compositions may take the form of tablets or lozenges formulated in conventional manner.

The compounds of the invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents and/or agents to adjust the tonicity of the solution. Alternatively, the active ingredient may be in powder form for reconstitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

For administration by inhalation the compounds according to the invention are conveniently delivered in the form of an aerosol spray presentation from pressurised packs, with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount. Capsules and cartridges of e.g. gelatine for use in an inhaler or insufflator may be formulated containing a powder mix of a compound of the invention and a suitable powder base such as lactose or starch.

A proposed dose of the compounds of the invention for oral, parenteral, rectal or buccal administration to man (of average body weight e.g. about 70 kg) for the treatment of migraine is 0.1 to 100 mg of the active ingredient per unit dose which could be administered, for example 1 to 4 times per day. It will be appreciated that it may be necessary to make routine variations to the dosage depending on the age and weight of the patient as well as the severity of the condition to be treated.

For oral administration a unit dose will preferably contain from 2 to 50 mg of the active ingredient. A unit dose for parenteral administration will preferably contain 0.2 to 5 mg of the active ingredient.

Aerosol formulations are preferably arranged so that each metered dose or "puff" delivered from a pressurized aerosol contains 0.2 mg to 2 mg of a compound of the invention, and each dose administered via capsules and cartridges in an insufflator or an inhaler contains 0.2 mg to 20 mg of a compound of the invention. The overall daily dose by inhalation will be within the range 1 mg to 100 mg. Administration may be several times daily, for example from 2 to 8 times, giving for example 1, 2 or 3 doses each time.

The compounds of the invention may, if desired, be administered in combination with one or more other therapeutic agents, such as analgesics, anti-inflammatory agents and anti-nauseants.

According to another aspect of the invention, compounds of general formula (I) and their physiologically acceptable salts and solvates (e.g. hydrates) may be prepared by the general methods outlined hereinafter. In the following processes, $R_1$, $R_2$, $R_3$, $R_4$, A, and Alk are as defined for the general formula (I) unless otherwise specified.

According to a general process (A), compounds of general formula (I) may be prepared by cyclisation of compounds of general formula (II):

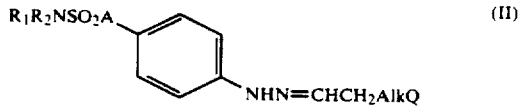

(II)

wherein Q is the group $NR_3R_4$ or a protected derivative thereof or a leaving group such as a halogen atom (e.q chlorine or bromine), or an acyloxy group which may be derived from a carboxylic or sulphonic acid, such as an acetoxy, chloroacetoxy, dichloroacetoxy, trifluoroacetoxy, p-nitrobenzoyloxy, p-toluenesulphonyloxy or methanesulphonyloxy group.

The reaction may conveniently be effected in aqueous or non-aqueous reaction media, and at temperatures of from 20° to 200° C., preferably 50° to 125° C.

Particularly convenient embodiments of the process are described below.

When Q is the group $NR_3R_4$ (or a protected derivative thereof) the process is desirably carried out in the presence of polyphosphate ester in a reaction medium which may comprise one or more organic solvents, preferably halogenated hydrocarbons such as chloroform, dichloromethane, dichloroethane, dichlorodifluoromethane, or mixtures thereof. Polyphosphate ester is a mixture of esters which may be prepared from phosphorus pentoxide, diethylether and chloroform according to the method described in "Reagents for Organic Synthesis", (Fieser and Fieser, John Wiley and Sons 1967).

Alternatively the cyclisation may be carried out in an aqueous or non-aqueous reaction medium, in the presence of an acid catalyst. When an aqueous medium is employed this may be an aqueous organic solvent such as an aqueous alcohol (e.g. methanol, ethanol or isopropanol) or an aqueous ether (e.g. dioxan or tetrahydrofuran) as well as mixtures of such solvents and the acid catalyst may be, for example, an inorganic acid such as concentrated hydrochloric or sulphuric acid or an organic acid such as acetic acid. (In some cases the acid catalyst may also act as the reaction solvent). In an anhydrous reaction medium, which may comprise one or more alcohols or ethers (e.g. as previously described) or esters (e.g. ethyl acetate), the acid catalyst will generally be a Lewis acid such as boron trifluoride, zinc chloride or magnesium chloride.

When Q is a leaving group, such as a chlorine or bromine atom, the reaction may be effected in an aqueous organic solvent, such as an aqueous alcohol (e.g. methanol, ethanol or isopropanol) or an aqueous ether (e.g. dioxan or tetrahydrofuran), in the absence of an inorganic acid catalyst, conveniently at a temperature of from 20° to 200° C., preferably 50° to 125° C. This process results in the formation of a compound of general formula (I) wherein $R_3$ and $R_4$ are both hydrogen atoms.

According to a particular embodiment of this process, compounds of general formula (I) may be prepared directly by the reaction of a compound of general formula (III):

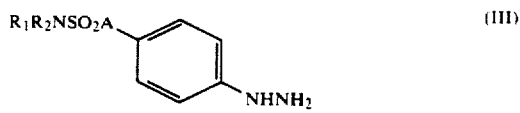

(III)

or a salt (e.g. the hydrochloride) thereof, with a compound of formula (IV):

OHCCH$_2$lkQ     (IV)

(wherein Q is as previously defined) or a salt or protected derivative thereof (such as an acetal, for example, a dialkyl or cyclic acetal e.g. formed with an appropriate alkyl orthoformate or diol or protected as a bisulphite addition complex), using the appropriate conditions as just described for the cyclisation of a compound of general formula (II) (The Fischer-Indole Synthesis, B. Robinson, p 488 —Wiley 1982). In this embodiment compounds of general formula (II) may be formed as intermediates and they may either be isolated prior to cyclisation or reacted in situ to form the desired compounds of general formula (I).

Compounds of general formula (II) may, if desired, be isolated as intermediates by reacting a compound of formula (III), or a salt or protected derivative thereof with a compound of formula (IV) or a salt or protected derivative thereof, in a suitable solvent, such as an aqueous alcohol (e.g. methanol) or an aqueous ether (e.g. dioxan) and at a temperature of, for example, from 20° to 30° C. If an acetal of a compound of formula (IV) is used it may be necessary to carry out the reaction in the presence of an acid (for example, acetic or hydrochloric acid).

The compounds of general formula (III) are novel compounds and form a further aspect of this invention. The compounds of general formula (III) may be prepared using conventional methods for preparing a hydrazine, for example reduction of the corresponding nitro compound to form the amino derivative, by catalytic hydrogenation, followed by reaction with sodium nitrite in the presence of a mineral acid (e.g. hydrochloric acid) to form a diazonium salt which is then reduced, e.g. with stannous chloride, to the desired hydrazine of formula (III).

A further general process (B) for preparing compounds of general formula (I) comprises reacting a compound of general formula (V):

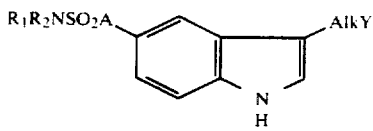

(wherein Y is a readily displaceable group) or a protected derivative thereof, with a compound of formula $R_3R_4NH$.

This displacement reaction may conveniently be carried out on those compounds of general formula (V) wherein the substituent group Y is a halogen atom (e.g. chlorine, bromine or iodine); a group $OR_5$ where $OR_5$ is, for example, an acyloxy group (which may be derived from a carboxylic or sulphonic acid) such as an acetoxy, chloroacetoxy, dichloroacetoxy, trifluoroacetoxy or p-nitrobenzoyloxy, p-toluenesulphonyloxy or methanesulphonyloxy group; or a group $N^\oplus R'R''R'''E^\ominus$, where R', R" and R'", which may be the same or different each represents a $C_{1-3}$ alkyl group and $E^\ominus$ represents an anion such as a halide ion e.g. a chloride, bromide or iodide ion.

The displacement reaction may conveniently be effected in an inert organic solvent (optionally in the presence of water), examples of which include alcohols e.g. ethanol; cyclic ethers, e.g. dioxan or tetrahydrofuran; acyclic ethers, e.g. diethylether; esters e.g. ethyl acetate; amides . e.g. N,N-dimethylformamide; and ketones e.g. acetone, methylethylketone or methylisobutylketone. The process may be carried out at a temperature of, for example, $-10$ to $+150°$ C., preferably 20° to 50° C.

The compounds of formula (V) wherein Y is a halogen atom may be prepared by reacting a hydrazine of formula (III) with an aldehyde (or a protected derivative thereof) of formula (IV) in which Q is a halogen atom, in an aqueous alcohol (e.g. methanol) or an aqueous ether (e.g. dioxan) containing an acid (e.g. acetic or hydrochloric acid) or by reacting a compound of general formula (V) wherein Y is a hydroxy group with the appropriate phosphorus trihalide or with N-bromosuccinimide and triphenylphosphine in tetrahydrofuran. The intermediate alcohol, wherein Y is a hydroxy group, may also be used to prepare compounds of formula (V), wherein Y is a group $OR_5$, by acylation with the appropriate activated species (e.g. an anhydride or sulphonyl chloride) using conventional techniques. The intermediate alcohol may be prepared by cyclisation of a compound of formula (II) wherein Q is a hydroxyl group (or a protected derivative thereof) under standard conditions.

Compounds of formula (V) wherein Y represents a group $NR'R''R''' E^\ominus$ may be prepared from the corresponding tertiary amine by reaction with an alkylating agent, for example as described in general process (E) hereinafter.

Compounds of general formula (I) may also be prepared by another general process (C) involving reduction of a compound of general formula (VI):

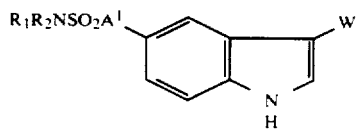

wherein W is a group capable of being reduced to give the required $AlkNR_3R_4$ group or to give a protected derivative of the $AlkN_3R_4$ group, and $A^1$ represents the group A as previously defined or a group capable of being reduced to form the group A,
or a salt or protected derivative thereof Groups $A^1$ which may be reduced to give the required group A include corresponding unsaturated groups such as $C_{2-5}$-alkenyl groups.

The required Alk and $NR_3R_4$ groups may be formed by reduction steps which take place separately or together in any appropriate manner.

Groups which may be reduced to the group Alk include corresponding unsaturated groups and corresponding groups containing one or more hydroxyl groups or carbonyl functions.

Groups which may be reduced to the group $NR_3R_4$ include nitro, azido, hydroxyimino, nitrile and amide groups.

Examples of groups represented by the substituent group W thus include $TNO_2$ (where T is Alk or an alkenyl group corresponding to the group Alk); $AlkN_3$; $AlkNR_3COR'_4$; $-COCONR_3R_4$; $(CHR_5)_xCHR_6CN$; $CHR_6COZ$; $(CHR_5)_xCR_6=NOH$; $CH(OH)CHR_6NR_3R_4$; $COCHR_6Z$ (where $R_5$ and $R_6$ which may be the same or different, each represents a hydrogen atom or a $C_{1-3}$ alkyl group, Z is an azido group $N_3$ or the group $NR_3R_4$ or a protected derivative thereof, x is zero or 1 and $R'_4$ is a hydrogen atom or a group such that $-CH_2R'_4$ is the group $R_4$, or $R'_4$ is the group $OR_c$ where $R_c$ is an alkyl or an aralkyl group).

Groups which may be reduced to form the group $NR_3R_4$ wherein $R_3$ and $R_4$ are both hydrogen include nitro, azido, hydroxyimino and nitrile groups. Reduction of a nitrile group yields the group $CH_2NH_2$ and thus provides a methylene group of the group Alk.

A compound of general formula (I) where $R_4$ is a hydrogen atom, may also be prepared by reduction of a corresponding compound of general formula (I) wherein $R_4$ is a benzyl group, for example with hydrogen in the presence of a catalyst e.g. 10% palladium on carbon.

The required $NR_3R_4$ group wherein $R_3$ and/or $R_4$ is other than hydrogen may be prepared by reduction of a nitrile $(CHR_5) CHR_6CN$ or an aldehyde $(CHR_5)_xCHR_6CHO$ (where $R_5$, $R_6$ and x are as previously defined) in the presence of an amine, $R_3R_4NH$.

A particularly suitable method for preparing a compound of formula (I) wherein $R_3$ and/or $R_4$ is other than hydrogen, is reductive alkylation of the corresponding compound wherein $R_3$ and/or $R_4$ represents hydrogen, with an appropriate aldehyde or a ketone (e.g. formaldehyde or acetone) in the presence of a suitable reducing agent. In some instances (e.g. for the introduction of the group $R_4$ where $R_4$ is methyl) the aldehyde (e.g. formaldehyde) may be condensed with the primary amine and the intermediate thus formed may subsequently be reduced using a suitable reducing agent.

The required $NR_3R_4$ group wherein $R_3$ and/or $R_4$ are other than hydrogen may also be prepared by reduction of a corresponding amide, for example, AlkNR$_3$COR'$_a$ (where R'$_4$ is as previously defined).

The reduction may be effected by conventional methods, for example by catalytic hydrogenation or using a reducing agent such as an alkali metal or alkaline earth metal borohydride or cyanoborohydride, or a metal hydride. The reduction may conveniently be effected in an organic reaction medium which may comprise one or more solvents. Suitable solvents include alcohols e.g. ethanol or propanol; cyclic ethers e.g. dioxan or tetrahydrofuran; acyclic ethers e.g. diethylether; amides e.g. dimethylformamide; and esters e.g. ethyl acetate, and nitriles e.g. acetonitrile.

It will be appreciated that the choice of reducing agent and reaction conditions will be dependent on the nature of the groups W and A$^1$.

Suitable reducing agents which may be used in the above process for the reduction of compounds of formula (VI) wherein W represents, for example, the groups TNO$_2$, AlkN$_3$, (CHR$_5$)$_x$CHR$_6$CN, (CHR$_5$)$_x$CR$_6$=NOH, CH(OH)CHR$_6$—NR$_3$R$_4$ (where T, R'$_4$, R$_5$ and R$_6$ and x are as previously defined) include hydrogen in the presence of a metal catalyst, for example Raney Nickel or a noble metal catalyst such as platinum, platinum oxide, palladium or rhodium, which may be supported, for example, on charcoal, kieselguhr or alumina. In the case of Raney Nickel, hydrazine may also be used as the source of hydrogen. This process may conveniently be carried out in a solvent such as an alcohol e.g. ethanol; an ether, e.g. dioxan or tetrahydrofuran; an amide, e.g. dimethylformamide; or an ester e.g. ethyl acetate, and at a temperature of from −10° to +50° C., preferably −5° to +30° C.

The reduction process may also be effected on compounds of general formula (VI) wherein W represents, for example, the groups TNO$_2$, CH(OH)CHR$_6$NR$_3$R$_4$ or COCHR$_6$ (where T, R$_6$ and Z are as previously defined), using an alkali metal or alkaline earth metal borohydride or cyanoborohydride e.g. sodium or calcium borohydride or cyanoborohydride which process may conveniently be carried out in an alcohol such as propanol or ethanol, or a nitrile such as acetonitrile, and at a temperature of from 10° to 100° C., preferably 50° to 100° C. In some instances the reduction using a borohydride may be carried out in the presence of cobaltous chloride.

Reduction of compounds of general formula (VI) wherein W represents, for example, the groups TNO$_2$, AlkN$_3$, AlkNR$_3$COR'$_4$, CHR$_6$COZ, (CHR$_5$)$_x$CR$_6$=NOH, CH(OH)CHR$_6$—NR$_3$R$_4$, —CO-CONR$_3$R$_4$ and COCHR$_6$Z (wherein T, R'$_4$, R$_5$, R$_6$, Z and x are as previously defined) may also be carried out using diborane or a metal hydride such as lithium aluminium hydride. This process may be carried out in a solvent, for example, an ether such as tetrahydrofuran, and conveniently at a temperature of from −10° to +100° C., preferably 50° to 100° C.

A particular embodiment of general process (C) includes the reduction of a compound of general formula (VI) wherein W is the group CHR$_6$CN, for example, by catalytic reduction with hydrogen in the presence of a catalyst such as palladium on charcoal or rhodium on alumina, optionally in the presence of an amine HNR$_3$R$_4$, or, to produce a compound wherein R$_3$ and R$_4$ are both hydrogen, using lithium aluminium hydride in the absence of an amine.

Suitable reducing agents which may be used in the reduction of the group A$^1$ include hydrogen in the presence of a metal catalyst. Appropriate metal catalysts and conditions for the process are as described for the reduction of the group W.

The starting materials or intermediate compounds of general formula (VI) may be prepared by analogous methods to those described in U.K. Published Patent Application No. 2035310 and "A Chemistry of Heterocyclic Compounds—Indoles Part II" Chapter VI edited by W. J. Houlihan (1972) Wiley Interscience, N.Y.

A compound of general formula (VI) wherein W is the group AlkNHCOR'$_4$ may be prepared by acylation of the corresponding unsubstituted amine using conventional techniques.

The Fischer-indole cyclisation process may be employed to prepare a compound of general formula (VI) wherein W is the group (CHR$_5$)$_x$CHR$_6$CN or CHR$_5$CHR$_6$NO$_2$ in conventional manner.

A compound of formula (VI) wherein A$^1$ is an alkenyl group containing 2 to 5 carbon atoms may be prepared by reacting a corresponding 5-halo indole of general formula (VII):

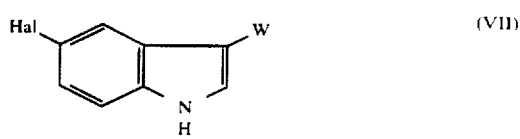

wherein W is as defined for general formula (VI) and Hal is a halogen atom e.g. bromine or iodine,
with an appropriate alkene of formula R$_1$R$_2$NSO$_2$(CH$_2$)$_p$CH=CH$_2$ (wherein p represents zero or 1 to 3) in the presence of a catalyst such as a palladium (II) salt, for example the acetate and a phosphine e.g. triphenylphosphine or tri-o-tolylphosphine, together with a tertiary nitrogen base such as triethylamine or tri-n-butylamine. The reaction may conveniently be effected in a solvent, e.g. acetonitrile, methanol or dimethylformamide, and at a temperature of from 75° to 160° C. Alternatively, compounds of formula (VI) may be prepared by reaction of an appropriate indole-5-carboxaldehyde of general formula (VIII):

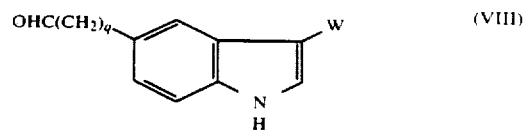

wherein W is as defined for general formula (VI) and q is an integer of 1 to 4,
with for, example, a suitable dialkylphosphonate, using standard conditions.

Compounds of general formula (I) may be prepared by another general process (D) which comprises reacting an indole of general formula (IX):

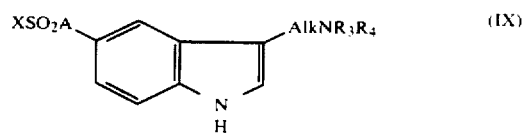

wherein X represents a leaving group with an amine of general formula (X):

(X)

Examples of suitable leaving groups X in the compound of general formula (IX) include a halogen atom (e.g. a fluorine, chlorine or bromine atom) or a group $OR_7$, where $R_7$ represents a hydrocarbyl group such as an aryl group, e.g. phenyl. The aryl group may be unsubstituted or substituted by one or more substituents such as halogen atoms; or nitro; cyano; amino; alkyl e.g. methyl; alkoxy e.g. methoxy; acyl, e.g. acetyl and alkoxycarbonyl e.g. ethoxycarbonyl groups. The leaving group represented by X is preferably a phenoxy group.

The reaction is conveniently carried out in the presence of a solvent and may be effected in an aqueous or non-aqueous reaction medium.

The reaction medium may thus comprise one or more organic solvents, such as ethers, e.g. dioxan or tetrahydrofuran; amides e.g. N,N-dimethylformamide or N-methylpyrrolidone; alcohols e.g. methanol or ethanol; esters e.g. ethyl acetate; nitriles e.g. acetonitrile; halogenated hydrocarbons e.g. dichloromethane; and tertiary amines e.g. triethylamine or pyridine, optionally in the presence of water. In some cases the amine of formula (X) may itself serve as the solvent.

If desired the aminolysis may be effected in the presence of a base, such as a tertiary amine (e.g. triethylamine or pyridine); an alkoxide (e.g. sodium t-butoxide) or a hydride (e.g. sodium hydride).

The reaction may conveniently be effected at a temperature of from $-20°$ C. to $+150°$ C.

The compounds of general formula (IX) are novel compounds and constitute a further aspect of this invention. They possess potent and selective vasoconstrictor activity, as described above for compounds of general formula (I).

The starting materials of general formula (IX) wherein X represents a group $OR_7$ may be prepared, for example by reduction of a compound of general formula (XI)

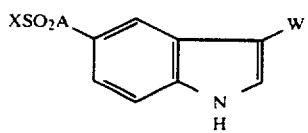

(XI)

(wherein W is as defined for general formula VI)) or a salt or protected derivative thereof.

The reduction may be carried out in analogous manner to the general process (C) and examples of suitable groups W and details of reaction conditions are given in connection with the general process (C).

A compound of formula (IX) wherein X represents a halogen atom may be prepared, for example by reacting the corresponding sulphonic acid derivative or a salt thereof with a halogenating agent such as a phosphorus halide or oxyhalide in an inert organic solvent e.g. phosphorus pentachloride in dichloromethane. A sulphonic acid of formula (IX), where X is OH, may be prepared for example by acid or base catalysed hydrolysis of an ester of formula (IX) (i.e. a compound wherein X represents the group $OR_7$).

Compounds of general formula (XI) may be prepared by analogous methods to those described in U.K. Published Patent Application No. 2035310 and "A Chemistry of Heterocyclic Compounds—Indoles Part II" Chapter VI edited by W. J. Hamilton (1972) Wiley Interscience, N.Y., as well as our copending U.K. Patent Application No. 8315564.

According to a further general process (E) a compound of formula (I) according to the invention, or a salt or protected derivative thereof may be converted into another compound of the invention using conventional procedures.

For example, a compound of general formula (I) wherein one or more of $R_1$, $R_2$, $R_3$ and $R_4$ are alkyl groups may be prepared from the corresponding compounds of formula (I) wherein one or more of $R_1$, $R_2$, $R_3$ and $R_4$ represent hydrogen atoms, by reaction with a suitable alkylating agent such as a compound of formula $R_xL$ where $R_x$ represents the desired $R_1$, $R_2$, $R_3$ or $R_4$ group and L represents a leaving group such as a halogen atom or a tosylate group, or a sulphate $(R_x)_2SO_4$. Thus, the alkylating agent may be for example an alkyl halide (e.g. methyl or ethyl iodide), alkyl tosylate (e.g. methyl tosylate) or dialkylsulphate (e.g. dimethylsulphate). The alkylation reaction is conveniently carried out in an inert organic solvent such as an amide (e.g. dimethylformamide), an ether (e.g. tetrahydrofuran) or an aromatic hydrocarbon (e.g. toluene) preferably in the presence of a base. Suitable bases include, for example, alkali metal hydrides, such as sodium or potassium hydride, alkali metal amides, such as sodium amide, alkali metal carbonates, such as sodium carbonate and alkali metal alkoxides such as sodium or potassium methoxide, ethoxide or t-butoxide. When an alkyl halide is employed as the alkylating agent the reaction may also be carried out in the presence of an acid scavenger such as propylene or ethylene oxide. A catalyst such as tetrabutylammonium fluoride may also be employed. The reaction may be conveniently effected at a temperature of $-20°$ C. to $+100°$ C.

Compounds of formula (I) wherein $R_1$ represents a $C_{3-6}$ alkenyl group, $R_2$ represents a $C_{3-6}$ alkenyl, phen($C_{1-4}$)alkyl or $C_{5-7}$ cycloalkyl group and/or one or both of $R_3$ and $R_4$ represents propenyl may be prepared similarly, using an appropriate compound of formula $R_xL$ or $(R_x)_2SO_4$.

According to another general process (F), a compound of general formula (I) according to the invention, or a salt thereof may be prepared by subjecting a protected derivative of general formula (I) or a salt thereof to reaction to remove the protecting group or groups.

Thus, at an earlier stage in the reaction sequence for the preparation of a compound of general formula (I) or a salt thereof it may have been necessary or desirable to protect one or more sensitive groups in the molecule to avoid undesirable side reactions. For example it may be necessary to protect the group $NR_3R_4$, wherein $R_3$ and/or $R_4$ represents hydrogen, by protonation or with a group easily removable at the end of the reaction sequence. Such groups may include, for example, aralkyl groups, such as benzyl, diphenylmethyl or triphenylmethyl; or acyl groups such as N-benzyloxycarbonyl or t-butoxycarbonyl or phthaloyl.

In some cases, it may also be desirable to protect the indole nitrogen with, for example, an aralkyl group such as benzyl.

Subsequent cleavage of the protecting group or groups may be achieved by conventional procedures. Thus an aralkyl group such as benzyl, may be cleaved by hydrogenolysis in the presence of a catalyst (e.g. palladium on charcoal) or sodium and liquid ammonia; an acyl group such as N-benzyloxycarbonyl may be removed by hydrolysis with, for example, hydrogen bromide in acetic acid or by reduction, for example by catalytic hydrogenation. The phthaloyl group may be removed by hydrazinolysis (e.g. by treatment with hydrazine hydrate) or by treatment with a primary amine (e.g. methylamine).

As will be appreciated, in some of the general processes (A) to (E) described previously it may be necessary or desirable to protect any sensitive groups in the molecule as just described. Thus, a reaction step involving deprotection of a protected derivative of general formula (I) or a salt thereof may be carried out subsequent to any of the previously described processes (A) to (E).

Thus, according to a further aspect of the invention, the following reactions (G) in any appropriate sequence may if necessary and/or desired be carried out subsequent to any of the processes (A) to (E):

(i) removal of any protecting groups; and
(ii) conversion of a compound of general formula (I) or a salt thereof into a physiologically acceptable salt or solvate (e.g. hydrate) thereof.

Where it is desired to isolate a compound of the invention as a physiologically acceptable salt, for example as an acid addition salt, this may be achieved by treating the free base of general formula (I), with an appropriate acid (e.g. succinic or hydrochloric acid) preferably with an equivalent amount in a suitable solvent (e.g. aqueous ethanol).

The starting materials or intermediate compounds for the preparation of the compounds according to this invention may be prepared by conventional methods analogous to those described in U.K. Published Patent Application No. 2035310.

As well as being employed as the last main step in the preparative sequence, the general methods indicated above for the preparation of the compounds of the invention may also be used for the introduction of the desired groups at an intermediate stage in the preparation of the required compound. Thus, for example, the required group at the 5-position may be introduced either before or after cyclisation to form the indole nucleus. It should therefore be appreciated that in such multi-stage processes, the sequence of reactions should be chosen in order that the reaction conditions do not affect groups present in the molecule which are desired in the final product.

The invention is further illustrated by the following examples. All temperatures are in °C. 'Hyflo' is a filtration aid. Reactivials are 4 ml stout-walled glass vials with a screw cap and teflon-faced disc, supplied by Pierce and Warriner (UK) Ltd. Chromatography was carried out either in the conventional manner using silica gel (Merck, Kieselgel 60 Art. 7734) or by 'flash' chromatography (W. C. Still, M. Kahn and A. Mitra, J. Org. Chem. 2923, 43, 1978 ) on silica (Merck (9385) and thin layer chromatography (t.l.c) on silica (Macherly-Nagel, Polygram) except where otherwise stated. The following abbreviations define the eluent used for chromatography and t.l.c.

(A) Methylene chloride-ethanol-0.88 ammonia 50:8:1
(B) Methylene chloride-ethanol-0.88 ammonia 100:8:1
(C) Methylene chloride-ethanol-0.88 ammonia 60:8:1
(D) Methylene chloride-ethanol-0.88 ammonia 25:8:1
(E) Methylene chloride-ethanol-0.88 ammonia 200:8:1
(F) Methylene chloride-ethanol-0.88 ammonia 750:10:1
(G) Methylene chloride-ethanol-0.88 ammonia 40:10:1
(H) Ether-cyclohexane 1:1
(I) Methanol-chloroform 5:95
(J) Ether
(K) Methylene chloride-ether 1:1
(L) Methylene chloride-ethanol-0.88 ammonia 75:8:1
(M) Isopropyl acetate
(N) Ethyl acetate-ether 1:1
(O) Methylene chloride-ethanol-0.88 ammonia 83.5:15:1.5
(P) Acetic acid-ethyl acetate 1:99
(Q) Ethyl acetate-cyclohexane 1:1
(R) Chloroform-methanol 50:1
(S) Chloroform-methanol 19:1
(T) Methylene chloride-ethanol-0.88 ammonia 150:8:1
(U) Methylene chloride-ethanol-0.88 ammonia 89:10:1
(V) Petroleum ether (bp60°-80°) -ethylacetate 2:1
(W) Cyclohexane-ether 2:1

Intermediates were routinely checked for purity by t.l.c. employing u.v. light for detection and spray reagents such as potassium permanganate ($KMnO_4$). In addition indolic intermediates were detected by spraying with aqueous ceric sulphate $Ce^{IV}$) and tryptamines by spraying with a solution of iodoplatinic acid (IPA) or ceric sulphate.

Proton ($^1H$) nuclear magnetic resonance (n.m.r) spectra were obtained either at 90 MHz using a Varian EM390 instrument or at 250 MHz using a Bruker AM or WM 250 instrument. s=singlet, d=doublet, t=triplet, q=quartet and m=multiplet.

PREPARATION 1

N-Methyl-4-nitrobenzeneethanesulphonamide hydrate (4:1)

A solution of 4-nitrobenzeneethanesulphonyl chloride (6.5 g) in methylene chloride (50 ml) was added dropwise, over a period of 0.25 h, to a rapidly stirred, ice-cold mixture of 40% aqueous methylamine (4 ml) in methylene chloride (20 ml). Further portions of 40% aqueous methylamine (1 ml) were added after stirring the suspension at 0° for a further 1 h and 0.5 h respectively. The suspension was then stirred at 0° for a further 0.5 h, before evaporating under reduced pressure to afford a solid (ca 7.0 g). This material was triturated with water (100 ml) and the solid collected by filtration, washed with petroleum-ether (b.p. 60°-80°) (50 ml) and dried to present the title compound as a powder (5.46 g) m.p. 126°-129°.

Analysis Found: C,43.35; H,4.9; N,11.1.
$C_9H_{12}N_2O_4S.0.25H_2O$ required C,43.45; H,5.1; N,11.3%.

PREPARATION 2

4-Amino-N-methylbenzeneethanesulphonamide

A solution of the product of Preparation 1 (7.9 g) in ethanol (150 ml) and dimethylformamide (10 ml) was added to a prereduced suspension of 10% palladium oxide on charcoal (1.0 g, 50% aqueous paste) in ethanol (50 ml) and hydrogenated at atmospheric pressure. After 2.75 h a further portion of catalyst (1.0 g) was added and the hydrogenation continued for another 2 h. A total of 2.14 l of hydrogen was absorbed. The catalyst and solvent were removed by filtration and rotary evaporation respectively, and the residual solid (8 g) extracted with boiling ethyl acetate (3×50 ml). The combined hot extracts were filtered and evaporated to dryness under reduced pressure to produce a solid. This material was triturated with petroleum-ether (b.p. 60°-80°) to present the title compound as a powder (5.2 g) m.p. 101°-105°.

PREPARATION 3

4-Hydrazino-N-methylbenzeneethanesulphonamide hydrochloride

The product of Preparation 2 (1.0 g) suspended in water (6 ml) was treated with conc. hydrochloric acid (1.0 ml) which precipitated the hydrochloric salt. The mixture was then cooled to −5° and treated with sodium nitrite (0.38 g) in water (2 ml) and stirred for 50 minutes keeping the temperature below −5°. The suspension was rapidly filtered to remove unreacted starting material and the filtrate added slowly to stannous chloride (5.0 g) in conc. hydrochloric acid (10 ml) at −5°. The solution was allowed to warm to 20° with vigorous stirring and the precipitate that formed was collected and washed with ether (50 ml) to give the title compound (1.2 g, 66% pure) as a powder. T.l.c. (A) Rf 0.8 (IPA)

PREPARATION 4

4-[2-(3-Cyanopropylidene)hydrazino]-N-methyl-benzeneethanesulphonamide

To a filtered solution of the product of preparation 3 (0.6 g, 67% pure) in water (13 ml) and dilute hydrochloric acid (2N, 0.25 ml) was added 3- cyanopropanal, dimethyl acetal (0.23 g) and the resulting solution stirred at room temperature for 24 h. The precipitated solid was filtered off, washed with water (2×30 ml), diethyl ether (50 ml) and dried to give the title compound as a powder (0.3 g), m.p. 96°-97°.

PREPARATION 5

3-(Cyanomethyl)-N-methyl-1H-indole-5-ethanesulphonamide

A suspension of the product of Preparation 4 (0.25 g) in polyphosphate ester (2.5 g) and chloroform (5 ml) was heated at reflux for 5 min and then poured onto ice. The resulting suspension was stirred for 20 min then extracted with chloroform (4×10 ml). The extract was washed with 8% sodium bicarbonate (10 ml) and water (10 ml), dried, filtered and evaporated to give an oil (0.35 g). This oil was chromatographed (J) to give the title compound (0.06 g) as an oil. T.l.C. (J) Rf 0.5 (u.v.).

EXAMPLE 1

3-(2-Aminoethyl)-N-methyl-1H-indole-5-ethanesulphonamide hemisuccinate hydrate

Method (I)

A solution of the product of Preparation 3 (1.019 g) in methanol (25 ml) and water (5 ml) was stirred at 50° and 4-chlorobutanal dimethylacetal (0.117 g) was added. After stirring for 0.75 h at 50° a further portion of 4-chlorobutanal dimethylacetal (0.117 g) was added and stirring at 50° continued for another 0.75 h. The solution was adjusted to pH4 by adding ammonium acetate (0.3 g) and refluxed for 5 h. Solvent was removed by evaporation under reduced pressure and the residue treated with saturated aqueous potassium carbonate solution (15 ml) and extracted with ethyl acetate (4×50 ml). The extracts were dried (MgSO$_4$) and concentrated to a gum (0.69 g). This material was chromatographed (B), (C) to give the tryptamine free base as a gum (0.072 g), which was taken up in hot isopropanol (2 ml) and treated with a hot solution of succinic acid (0.0151 g) in hot isopropanol (0.5 ml). After adding absolute alcohol (ca. 1.0 ml) to the boiling mixture the solution was allowed to cool. The solid that crystallised out was collected by filtration, washed with anhydrous ether and dried to present the title compound as a powder (0.046 g) m.p. 133°-138°.

Analysis Found: C,50.8;H,6.1;N,11.4.
C$_{13}$H$_{19}$N$_3$O$_2$S.0.5C$_4$H$_6$O$_4$.0.1C$_3$H$_8$O.0.75 H$_2$ 0 requires: C,51.1; H, 6.8; N,11.7%.
N.m.r δ(CD$_3$SOCD$_3$)2.65(3H,s,MeNHSO$_2$)2.7–3.4 (8H,m,NHSO$_2$CH$_2$CH$_2$ and CH$_2$CH$_2$NH$_2$),6.8–7.5(4H,m,aromatic).

EXAMPLE 2

N-Methyl-3-[2-(methylamino)ethyl-1H-indole-5-ethanesulphonamide compound with succinic acid and water (6:4:3)

A solution of the product of Preparation 5 (0.45 g) in ethanolic methylamine (25% w/v, 25 ml) was hydrogenated over 10% palladium oxide on charcoal (0.8 g, 50 % aqueous paste) pre-reduced in ethanol (5 ml). The catalyst was removed by filtration through 'hyflo' and the filtrate concentrated to give a gum (0.45 g) which was dissolved in hot isopropanol (5 ml) and treated with a solution of succinic acid (0.093 g) in methanol (0.5 ml). A thick gum precipitated out. The reaction mixture was concentrated in vacuo (ca. 1 ml of solvent). The solvent was decanted off and the residual gum was triturated with diethyl ether (3×25 ml to give a solid which was filtered off and dried to give the title compound as a powder 0.33 g, m.p. 62°-65°.

Analysis Found: C,52.5;H,6.8;N,11.0.
C$_{14}$H$_{21}$N$_3$O$_2$S.0.66C$_4$H$_6$O$_2$.0.5H$_2$0 requires C,52.3;H,7.2;N,10.9%.
nmr spectrum agreed with that of Example 3.

EXAMPLE 3

N-Methyl3-[2-(methylamino)ethyl]-1H-indole-5-ethanesulphonamide hydrochloride hydrate In a similar manner to Example 2 the product of Preparation 5 (0.70 g) was hydrogenated, filtered and the filtrate concentrated to give a gum (0.7 g) which was purified by flash chromatography (T, 3 cm dia. col). The resulting gum (0.3 g) was extracted with ethyl acetate (20 ml), filtered and treated with an excess of ethereal hydrogen chloride. The solid was collected by filtration, washed with ether (25 ml) and dried (15 h, 20°, vacuum pistol) to give the title compound as a powder, (0.24 g) m.p. 151°-154°.

Analysis Found: C,49.3;H,6.6;N,11.8.
C$_{14}$H$_{21}$N$_3$O$_2$S.HCl.0.5H$_2$O.0.07C$_4$H$_8$O$_2$ requires C,49.3;H,6.8;N,12.1.
nmr δ(CD$_3$SOCD$_3$) 2.50 (3H, s NHMe) 2.66 (3H, s SO$_2$NHMe) 2.9–3.5 (8H, m CH$_2$CH$_2$SO$_2$NH and CH$_2$CH$_2$NH) and 6.9–7.5 (m aromatic).

EXAMPLE 4

3-(2-Aminoethyl)-N-(phenylmethyl)-1H-indole-5-ethanesulphonamide, compound with creatinine, sulphuric acid and water (1:1:1:1)

(i)

4-Nitro-N-(phenylmethyl)benzeneethanesulphonamide

Benzylamine (9.83 ml) in dichloromethane (10 ml) was added dropwise to an ice-cold, stirred solution of 4-nitrobenzeneethanesulphonyl chloride (7 g) in dichloromethane (250 ml). After 18 h the reaction mixture was washed with water (3×40 ml), brine (3×25 ml) dried (Na₂SO₄) and evaporated to dryness and the product recrystalised from isopropanol (50 ml) to give the title compound as needles (6 g) m.p. 125°–127°.

(ii)

4-Amino-N-(phenylmethyl)benzeneethanesulphonamide

A suspension of the product of Stage (i) (11 g) in methanol (120 ml) was hydrogenated over pre-reduced 10% palladium oxide on charcoal (50% aq. paste, 2 g) at room temperature and pressure until hydrogen uptake (1.99 l) ceased. The catalyst was filtered off and the filtrate evaporated to dryness to give a solid which was purified by cryatallisation from methanol to give the title compound as a solid (3.2 g) m.p. 1.09°–111°.

T.l.c. (E) Rf 0.4 (Ce$^{IV}$).

(iii)

4-Hydrazino-N-(Phenylmethyl)benzeneethanesulphonamide, hydrochloride

A solution of sodium nitrite (0.25 g) in water (1.9 ml) was added to a cold suspension of the product of Stage (ii) (1 g) in a mixture of conc. hydrochloric acid (7.5 ml) and water (4.5 ml) keeping the temperature below −5° C. This mixture was stirred at −5° for 50 min and the remaining solid removed by filtration. The ice-cooled filtrate was then added slowly to a solution of stannous chloride dihydrate (3.5 g) in conc. hydrochloric acid (7.5 ml) keeping the temperature below 0°. After the addition the mixture was stirred at room temperature for 3 h and the solid collected, washed with diethyl ether (3×50 ml) and dried to give the title compound as a powder (0.46 g).

T.l.c. (B) Rf 0.43(IPA).

(iv)

3-(2-Aminoethyl)-N-(phenylmethyl)-1H-indole-5-ethanesulphonamide compound with creatinine, sulphuric acid and water (1:1:1:1)

4-Chlorobutanal dimethyl acetal (0.18 g) was added to a stirred solution of the product of Stage (iii) (0.45 g) in a mixture of ethanol (18 ml) and water (4.5 ml) and the mixture heated at reflux for 2 h. The cooled mixture was evaporated to dryness and the residue chromatographed twice (A) to give the tryptamine as an oil (70 mg) which was dissolved in a boiling mixture of ethanol (5.6 ml) and water (0.7 ml) and treated with an aqueous solution of creatinine and sulphuric acid (1:1, 2M, 0.1 ml). On cooling the title compound was deposited as a solid (96 mg) m.p. 217°–220° (softens at 210°).

Analysis Found: C,47.0;H,5.9;N,14.2.

$C_{19}H_{23}N_3O_2S.C_4H_7N_3O.H_2SO_4.H_2O$ requires C,47.1;H,5.8;N,14.3%.

N.m.r. δ(CD₃SOCD₃)2.9–3.3)8H,m,NHSO₂CH₂CH₂ and CH₂CH₂NH₂), 4.24 (2H,s,CH₂NHSO₂), 6.85–7.5(m, aromatic).

EXAMPLE 5

3-[2-(Ethylamino)ethyl]-N-methyl-1H-indole-5-ethaneasulphonamide hemisuccinate hemihydrate

Method (I)

A suspension of 10% palladium oxide on carbon (0.8 g of a 50% paste with water) in ethanol (5 ml) was prehydrogenated for 20 min. To this was added the product of Preparation 5 (0.40 g) in ethanolic ethylamine (25 ml) and the resulting suspension was stirred for 2 h at 20°. The suspension was filtered through hyflo and the filtrate concentrated in vacuo to give an oil (0.38 g) which was chromatographed twice (B) to give the tryptamine as an oil (0.114 g). The oil was dissolved in absolute ethanol (2 ml) and to this was added succinic acid (22.5 mg) in ethanol. The crystals were collected by filtration to give the title compound (70 mg) m.p. 148°–150°.

Analysis Found: C,54.5;H,7.1;N,10.9.

$C_{15}H_{23}N_3O_2S.0.5C_4H_6O_4.0.5H_2O$ requires C,54.1;H,7.2;N,11.1%.

N.m.r. δ(CD₃SOCD₃)1.11(3H,t,NHCH₂Me),2.64(3H,s,MeNHSO₂). 2.78(2H,q, NHCH₂CH₃),2.85–3.4(8H,m,NHSO₂CH₂CH₂, and CH₂CH₂NH)6.9–7.5(4H,m, aromatic).

Method (II)

(i)

N-[2-[5-[2-[(Methylamino)sulphonyl]ethyl]-1H-indol-3-yl]ethyl]acetamide

A solution of the product of Example 1 (0.3 g) in anydrous tetrahydrofuran (15 ml) was treated with acetic anhydride (0.084 ml) and stirred at room temp. for 1.5 h. The resulting solution was then evaporated to dryness and the residue dissolved in ethyl acetate (20 ml). The ethyl acetate solution was washed with aqueous 8% sodium bicarbonate (20 ml) and then with water (10 ml) dried and evaporated under reduced pressure to produce a gum (0.45 g). This material was chromatographed (A) to give the title compound as a gum (0.389 g).

T.l.c. (A) Rf 0.6.

(ii)

3-[2-(Ethylamino)ethyl]-N-methyl-1H-indole-5-ethanesulphonamide hemisuccinate

A solution of the product of Stage (i) (0.3 g) in anhydrous tetrahydrofuran (THF) (16 ml) was added to a stirred mixture of lithium aluminium hydride (0.353 g) in THF (20 ml) under an atmosphere of nitrogen. The resulting suspension was stirred for 2 h at reflux and then allowed to stand overnight at room temp. before refluxing for a further 1 h. After cooling the reaction (ice-bath), water (10 ml) was added and the resulting mixture filtered through hyflo. The filtrate was extracted with ethyl acetate (4×25 ml) and the extracts dried (MgSO₄) and evaporated to produce a gum (0.187 g). This material was chromatographed (A) to give the free base as a gum (0.12 g). A solution of the free base (0.12 g) in hot absolute alcohol (2 ml) was treated with a solution of succinic acid (0.0229 g) in methanol (0.75 ml). The resulting solution was evaporated to dryness to yield a foam which was triturated with anhydrous ether to present the title compound as a hygroscopic foam (0.068 g) m.p. 65°–75°, shown by n.m.r. and t.l.c.(B, Rf 0.25) to be identical with the product of Method (I):

EXAMPLE 6

3-(3-Aminopropyl)-N-methyl-1H-indole-5-ethanesulphonamide compound with oxalic acid and ethanol (1:1.2:0.83)

(i)

3-[3-(1,3-Dihydro-1,3-dioxo-2H-isoindol-2-yl)propyl]-N-methyl-1H-indole-5-ethanesulphonamide A mixture of the product of Preparation 3 (68% pure; 2.5 g) and 2-(5,5-dimethoxypentyl)-1H-isoindole-1 3(2H)-dione (83% pure; 3.15 g) in 10% aqueous acetic acid (200 ml) was stirred at room temperature for 1.75 h, and then at reflux for 3.5 h. The mixture was allowed to cool, extracted with chloroform (3×100 ml) and the combined extracts washed with 2N hydrochloric acid (100 ml) add 2N sodium carbonate (100 ml), dried ($Na_2SO_4$) and concentrated in vacuo. Short-path column chromatography (F, 15 cm dia. col.) of the residual gum (4.33 g) afforded a solid (0.43 g). Crystallisation of this solid from a mixture of chloroform and methanol (1:1, 10 ml) gave the title compound as a solid (0.25 g) m.p. 169°-169.5°

T.l.c. (F) Rf 0.19 ($Ce^{IV}$).

(ii)

3-(3-Aminopropyl)-N-methyl-1H-indole-5-ethanesulphonamide compound with oxalic acid and ethanol (1:1.2:0.83)

Hydrazine hydrate (0.34 ml) was added to a refluxing suspension of the product of Stage (i) (250 mg), in ethanol (10 ml), the resultant solution stirred for 4 h, and then allowed to cool. The suspension was concentrated in vacuo and the residual solid partitioned between 2N sodium carbonate (25 ml) and ethyl acetate (3×25 ml). The combined organic extracts were then dried ($Na_2SO_4$) and concentrated in vacuo. Flash column chromatography (G, 1 cm. dia. col.) of the residue (110 mg) afforded a gum (98 mg) which was dissolved in refluxing absolute ethanol (3 ml) and a solution of oxalic acid (30 mg) in absolute ethanol (0.5 ml) was added. The gummy suspension was warmed gently to obtain a solution and allowed to cool with stirring. The resultant suspension was filtered and the solid washed with absolute ethanol (3×1 ml) and dried in vacuo at 50° for 18 h to give the title compound as a solid (110 mg) m.p. 160°-162°(softens>98°)

Analysis Found: C,49.2;H,6.85;N,9.6.

$C_{14}H_{21}N_3O_2S.1.2C_2H_2O_4.0.83C_2H_6O$ requires C,49.1;H,6.5;N,9.5%.

N.m.r. δ($CD_3SOCD_3$)1.90(2H, m, $CH_2CH_2CH_2NH_2$),2.62(3H,d,$MeNHSO_2$), 2.73 and 2.82(4H,t and t, $CH_2CH_2CH_2NH_2$),2.95–3.3(4H,m,N-$HSO_2CH_2CH_2$), 6.95–7.45 (4H,m,aromatic).

EXAMPLE 7

3-(2-Aminopropyl)-N-methyl-1H-indole-5-ethanesulphonamide hydrochloride (i) 4-Nitropentanal To a cold solution of acrolein (45 ml) and nitroethane (120 ml), in ether (750 ml) was added a solution of tri-n-butylphosphine (15 drops) in ether (60 ml) so that the temperature did not exceed −8°. The reaction was stirred for a further 30 min, methyl iodide (2 drops) was added and the ether was removed by evaporation in vacuo at 40°. The residue was purified by column chromatography (H) to give an oil (6.7 g) which was distilled at 130°-135°, 3 mm Hg to give the title compound as an oil (1.5 g).

T.l.c. (H) Rf 0.3 ($KMnO_4$).

(ii)

N-Methyl-4-[2-(4-nitropentylidene)hydrazino]benzeneethanesulphonamide

To a filtered solution of the product of Preparation 3 (3.678 g of 67% purity) in water (20 ml) was added dropwise 4-nitropentanal (1.5 g) and the reaction was monitored by t.l.c. The reaction mixture was extracted with chloroform (200 ml), dried ($MgSO_4$) and evaporated in vacuo to give the title compound (2.8 g) as an oil which was used without further purification in the next stage.

T.l.c. (I) Rf 0.4 ($Ce^{IV}$).

(iii)

N-methyl-3-(2-nitropropyl)-1H-indole-5-ethanesulphonamide

A solution of the product of Stage (ii) (2.8 g) polyphosphate ester (28 g) and chloroform (50 ml) was heated at reflux for 5 min and then poured onto ice (100 g). The resulting suspension was stirred for 30 min, and extracted with chloroform (3×100 ml). The organic extract was washed with 8% sodium bicarbonate solution (2×100 ml), water (2×100 ml), dried ($MgSO_4$) filtered and evaporated to give an oil (5.2 g). The oil was purified by flash chromatography (J, 8 cm dia. col.) to give the title compound (0.47 g) as an oil.

T.l.c. (J) Rf 0.8 ($KMnO_4$, IPA).

Analysis Found: C,51.5;H,5.6;N,12.7.

$C_{14}H_{19}N_3O_4S$ requires C,51.7;H,5.9;N,12.9.

(iv)

3-(2-Aminopropyl)-N-methyl-1H-indole-5-ethanesulphonamide hydrochloride

A solution of the product of Stage (iii) (0.43 g) in ethanol (50 ml), was hydrogenated over pre-reduced 10% palladium oxide on charcoal (0.4 g) for 75.5h at atmospheric pressure and temperature. The reaction mixture was filtered and evaporated in vacuo to give an oil (0.27 g) which was chromatographed (A, 3 cm dia. col.) to give the tryptamine as an oil (0.23 g). A solution of the oil in ethanol (5 ml) was treated with ethereal hydrogen chloride (pH 3), the salt filtered off and dried to give the title compound as a solid (0.2 g) m.p. 211°-212°.

Analysis Found: C,50.4;H,6.7;N,12.2

$C_{14}H_{21}N_3O_2S.HCl.O.18H_2O$ requires C,50.2;H,6.7;N,12.5.

N.m.r. δ($CD_3SOCD_3$)1.19(3H,d,-CH—$CH_3$),2.64(3H,d,$SO_2NHCH_3$),2.75–3.5(7H,m,$CH_2CH(Me)NH_2$ and $CH_2CH_2SO_2NH$)-,7–7.55(5H,m,aromatic+$NHSO_2$).

EXAMPLE 8

3-(2-Aminoethyl)-N,N-dimethyl-1H-indole-5-ethanesulphonamide compound with creatinine and sulphuric acid (1:1:1)

(i) 2-(1H-Indol-5-yl)-N,N-dimethylethenesulphonamide

A mixture of 5-bromoindole (7.7 g), N,N-dimethylethenesulphonamide (5.3 g) triethylamine (15 ml), acetonitrile (5 ml), palladium (II) acetate (0.35 g) and tri-o-tolylphosphine (0.95 g) was heated at 100° C. in an autoclave for 3 h. The resulting cooled mixture was partitioned between hydrochloric acid (2N, 300 ml) and ethyl acetate (2×150 ml). The combined extracts were dried (Na₂SO₄) and evaporated in vacuo. The residue was purified by 'flash' chromatography (V, 7 cm col.) to give the title compound as a crystalline solid (3.8 g) m.p. 148°–150° C.

(ii) N,N-Dimethyl-1H-indole-5-ethanesulphonamide

A solution of the product of Stage (i) (3.8 g) in ethanol (400 ml) was hydrogenated at room temperature and pressure over 10% palladium oxide on charcoal (50% aq. paste, 0.5 g), for 2 h. The catalyst was filtered off and replaced with a fresh batch (50% aq. paste, 0.5 g) and hydrogenation continued for a further 1 h. The catalyst was filtered off and the filtrate evaporated in vacuo to give a solid (2.8 g) which was recrystallised from a mixture of ethyl acetate and hexane to give the title compound as a solid (2.0 g) m.p. 125°–127°.

(iii) 3-[(Dimethylamino)methyl]-N,N-dimethyl-1H-indole-5-ethanesulphonamide

A solution of the product of Stage (ii) (0.8 g) in acetonitrile (40 ml) containing N,N-dimethylmethyleneammonium chloride (0.6 g) was stirred at room temperature for 3 h. The resulting solution was partitioned between sodium carbonate (2N, 50 ml) and ethyl acetate (2×50 ml). The organic extracts were dried (Na₂SO₄) and evaporated in vacuo to give a solid. Trituration with ether gave the title compound as a solid (0.9 g) m.p. 156°–159°.

(iv) 3-(Cyanomethyl)-N,N-dimethyl-1H-indole-5-ethanesulphonamide

Iodomethane (1.1 ml) was added to a stirred solution of the product of Stage (iii) (2.7 g) in dry dimethylsulphoxide (30 ml) and the resulting solution stirred at room temperature for 10 min. Potassium cyanide (2.7 g) was added, and the resulting mixture stirred at room temperature overnight. The mixture was partitioned between sodium carbonate, (2N, 300 ml) and ethyl acetate (2×100 ml). The combined extracts were dried (Na₂SO₄) and evaporated in vacuo to give an oil which was purified by 'flash' chromatography (J, 5 cm col.) to give the title compound as a solid (1.3 g) m.p. 105°–107°.

(v) 3-(2-Aminoethyl)-N,N-dimethyl-1H-indole-5-ethanesulphonamide, compound with creatinine and sulphuric acid (1:1:1)

A solution of the product of Stage (iv) (0.2 g) in ethanol (40 ml) containing concentrated hydrochloric acid (0.1 ml) was hydrogenated at room temperature and pressure over 10% palladium oxide on charcoal (50% aq. paste, 0.2 g) for 24 h. The catalyst was filtered off, and the filtrate evaporated in vacuo to give an oil. The oil was partitioned between hydrochloric acid (2N, 20 ml) and ethyl acetate (20 ml). The aqueous layer was basified (Na₂CO₃) and extracted with ethyl acetate (2×20 ml). The combined extracts were dried (Na₂SO₄) and evaporated in vacuo to give the tryptamine as an oil (0.05 g) which was dissolved in a hot mixture of ethanol (9 ml) and water (1 ml), and a solution of creatinine in sulphuric acid (2M, 1:1 0.08 ml) added. Filtration of the cooled mixture gave the title compound as a solid (0.05 g) m.p. 223°–225° (dec.).

Analysis Found: C,39.9;H,6.2;N,15.85.

C₁₄H₂₁N₃O₂S.C₄H₇N₃O.H₂SO₄.2H₂O requires C,39.9;H,6.3;N,15.5%.

N.m.r. δ(CD₃SOCD₃)2.82(6H,s,SO₂NMe₂),2.9–3.4(8H,m,CH₂CH₂SO₂N and CH₂CH₂NH₂),7.0–7.55(4H, m,aromatic).

EXAMPLE 9

3-[2-(Dimethylamino)ethyl]-N-methyl-1H-indole-5-ethanesulphonamide, compound with creatinine, sulphuric acid and water (1:2:1.5:2)

A solution of the product of Preparation 5 (0.4 g) in ethanolic dimethylamine (33% w/w, 25 ml) was hydrogenated at room temperature and pressure over prereduced 10% palladium oxide on charcoal (50% aq. paste, 0.7 g) for 3 h. The catalyst was filtered off and the filtrate concentrated in vacuo to give an oil (0.35 g), which was purified by flash chromatography (B, 8 cm dia. col.). The resulting oil (0.25 g) was dissolved in hot ethanol (20 ml) and water (2.5 ml) and treated with an aqueous solution of creatinine and sulphuric acid (1:1, 2M, 0.4 ml) and cooled to 5° to deposit the title compound as a solid (0.22 g), m.p. 193°–197°.

Analysis Found: C,38.2;H,5.6;N,17.0.

C₁₅H₂₃N₃O₂S.2C₄H₇N₃O.1.5H₂SO₄.2H₂O requires C,38.45;H,6.05;N,17.5%.

n.m.r. characteristics agreed with those in Example 10.

EXAMPLE 10

3-[2-(Dimethylamino)ethyl]-N-methyl-1H-indole-5-ethanesulphonamide hydrochloride Method (I)

A suspension of 10% palladium oxide on charcoal (14 g, 50% paste with water) in ethanol (100 ml) was prehydrogenated for 20 min. To this was added the product of Preparation 5 (8 g) in ethanolic dimethylamine (33% w/v, 400 ml) and the resulting suspension stirred for 18 h at 20° under an atmosphere of hydrogen. The suspension was filtered through hyflo and evaporated to give an oil (8.4 g) which was purified by flash chromatography (8 cm dia. col.) to give the tryptamine as an oil (6.0 g). The oil was extracted with diethyl ether (2 l) and ethyl acetate (200 ml) to leave a residue (0.5 g) which was discarded. The organic extracts were combined, evaporated in vacuo and dissolved in analar ethyl acetate (300 ml). Ethereal hydrogen chloride was added dropwise with rapid stirring. The resulting crystals were collected by filtration, washed with ether (100 ml) and dried at 60° for 16 h to give the title compound (5.5 g) m.p. 137°–139°

Analysis Found: C,51.8;H,6.7;N,11.9.

C₁₅H₂₃N₃O₂S. HCl requires C,52.1;H,7.0;N,12.15.

N.m.r. (CD₃SOCD₃)2.65(3H,d,MeNHSO₂),2.84(6H,s,NMe₂),3.0–3.45(8H,m, CH₂CH₂NMe₂ and NHSO₂CH₂CH₂),7.0–7.6(5H,m,aromatic+N-HSO₂).

Method (II)

(i) 5-[2-[(Methylamino)sulphonyl]ethyl]-1H-indole-3-acetic acid

A solution of the product of Preparation 5 (0.3 g) in ethanol (15 ml) and water (15 ml) containing potassium hydroxide (1.5 g) was heated at reflux for 18 h, cooked, and the ethanol evaporated in vacuo. The residue was partitioned between hydrochloric acid (2N, 50 ml) and ethyl acetate (2×50 ml). The combined extracts were dried (Na$_2$SO$_4$) and evaporated in vacuo. The residue was purified by 'flash' chromatography (M, 3 cm dia. col.) to give the title compound as an oil which crystallised on standing (0.1 g) m.p. 123°-125° C.

(ii)
3-(2-Hydroxyethyl)-N-methyl-1H-indole-5-ethanesulphonamide

A solution of the product of Stage (i) (1.0 g) in dry tetrahydrofuran (THF, 50 ml) containing lithium aluminum hydride (1.0 g) was heated at reflux, under nitrogen, for 6 h. The resulting mixture was cooled, and excess reducing agent decomposed by adding excess 10% aq. THF. The resulting mixture was partitioned between sodium carbonate (2N, 50 ml) and ethyl acetate (2×50 ml). The combined extracts were dried (Na$_2$SO$_4$) and evaporated in vacuo to give an oil which was purified by 'flash' chromatography (N, 4 cm dia. col.) to give the title compound as an oil (0.35 g)

T.l.c. (N) Rf 0.4 (Ce$^{IV}$).

(iii)
3-[2-(Dimethylamino)ethyl]-N-methyl-1H-indole-5-ethanesulphonamide hydrochloride A solution of triphenylphosphone (0.44 g) in tetrahydrofuran (THF, 3 ml) was added, in one portion, to a solution of N-bromosuccinimide (NBS, 0.3 g) in THF (5 ml) giving a precipitate. A solution of the product of Stage (ii) (0.39 g) in THF (10 ml) was added, and the mixture stirred at room temp. for 18 h. A solution of dimethylamine (33% w/v in ethanol, 20 ml) was added, and the resulting solution stirred at room temp. for 3 days then evaporated in vacuo and the residue partitioned between hydrochloric acid (2N, 25 ml) and ethyl acetate (2×25 ml). The aqueous layer was basified (Na$_2$CO$_3$) and extracted with ethyl acetate (2×25 ml). The combined extracts were dried (Na$_2$SO$_4$) and evaporated in vacuo to give an oil which was purified by 'flash' chromatography (A, 4 cm dia. col.) to give pure free base as an oil (0.08 g). This oil was dissolved in absolute ethanol (5 ml) acidified with ethereal hydrogen chloride, and diluted with dry ether to precipitate the title compound as a hygroscopic solid which was shown by n.m.r. and t.l.c. (A, Rf 0.4) to be identical with the product of Method (I).

Method (III)

(i)
4-[2-[4-(Dimethylamino)butylidene]hydrazino]-N-methylbenzene-ethanesulphonamide 4,4-Dimethoxy-N,N-dimethylbutanamine (0.87 g) was added to a solution of the product of Preparation 3 (2.0 g; purity ca 65%) in water (40 ml), 2N hydrochloric acid (2.2 ml) was added, and the mixture (pH ~ 1.5) was stirred at room temp. under nitrogen for 4 h. Further acetal (160 mg) was added, and stirring was continued at room temp. for 1 h. The mixture was basified with 8% aqueous sodium bicarbonate (20 ml) and extracted with chloroform (3×70 ml); the aqueous layer was saturated with sodium chloride and extracted again with chloroform (3×120 ml). The combined organic layers were dried (MgSO$_4$) and evaporated to give an oil (2.25 g). A sample (113 mg) of the oil was purified by flash chromatography (U, 2 cm dia. col. ) to give the title compound as an oil (71 mg)

T.l.c. (U) RF 0.4 (IPA).

(ii)
3-[2-(Dimethylamino)ethyl]-N-methyl-1H-indole-5-ethanesulphonamide hydrochloride The product of Stage (i) (2.1 g) was heated under reflux with polyphosphate ester (10.5 g) in chloroform (40 ml) with stirring under nitrogen for 8 min. The mixture was poured onto ice, stirred for 1.75 h, basified with 2N sodium carbonate (100 ml), and extracted with chloroform (3×250 ml). The organic layers were dried (MgSO$_4$) and evaporated to give an oil (1.96 g). Partial purification by flash chromatography (O, 3 cm dia. col) gave an oil (0.726 g); further purification by short path chromatography gave the pure free base also as an oil (0.56 g). The oil was warmed with analar ethyl acetate (30 ml), and a portion (12 ml) of the solution was filtered and acidified with ethereal hydrogen chloride (to pH2). The resulting precipitate was washed by decanting with dry ether and dried in vacuo (60°, 17 h) to present the title compound as a hygroscopic solid (129 mg) which was shown by n.m.r. and t.l.c. (O, Rf 0.25) to be identical with the product of Method (I).

Method (IV)

(I)
N,N-Dimethyl-5-[2-[(methylamino)sulphonyl]ethyl]-1H-indole-3-acetamide A mixture of N,N'-carbonyl-diimidazole (0.57 g) and the product of Method (II) Stage (i) (0.9 g) in freshly distilled tetrahydrofuran (25 ml) was stirred at room temperature for 1 h. The mixture was then cooled to 0° C. and dimethylamine (2 ml) added. After stirring (at 0° C.) for 2 h the solvent was removed under reduced pressure. The residue was chromatographed (P) to give the title compound as an oil (0.53 g). T.l.c. (P) RF 0.25 (Ce$^{IV}$).

(ii)
3-[2-(Dimethylamino)ethyl]-N-methyl-1H-indole-5-ethanesulphonamide hydrochloride A solution of the product of Stage (i) (0.15 g) in freshly distilled tetrahydrofuran (5 ml) was added to a cold (0°) suspension of lithium aluminium hydride (87 mg) in freshly distilled tetrahydrofuran (10 ml) under nitrogen and the mixture heated at reflux for 2 h. The cooled mixture was added to saturated potassium carbonate solution (15 ml) and the organic phase separated. The aqueous phase was extracted with ethanol (20 ml) and the combined organic phases evaporated under reduced pressure to give an oil which was dissolved in absolute alcohol (1 ml) and ethereal hydrogen chloride solution (3 ml) added. The solvent was removed by evaporation under reduced pressure and the residue triturated with ethyl acetate- cyclohexane (1:1) to give the title compound (0.1 g) m.p. 132°-134°, which was shown by t.l.c. (B, Rf 0.1) and n.m.r. to be identical with the product of Method (I).

Method (V)

(i) (E)-2-(1H-indol-5-yl)-N-methylethenesulphonamide

A mixture of 5-bromoindole (6.6 g), N-methylethenesulphonamide (5.1 g) palladium (II) acetate (75 mg), tri-o-tolylphosphine (0.2 g), triethylamine (12 ml), and acetonitrile (5 ml) was heated at 100° in an autoclave for 3 h. The reaction mixture was cooled and partitioned between hydrochloric acid (1N, 300 ml) and ethyl acetate (2×150 ml). The combined extracts were dried, (Na₂SO₄) and evaporated in vacuo to give an oil which was purified by 'flash' chromatography (Q, 7 cm dia. col.) to give the title compound as a solid (2.3 g) m.p. 164√-166°.

T.l.c. (Q) Rf 0.25 (Ce^{II}).

(ii) N-Methyl-1H-indole-5-ethanesulphonamide

A solution of the product of Stage (i) (2.3 g) in a mixture of ethyl acetate (30 ml) and methanol (15 ml) was hydrogenated at room temperature and pressure over 10% palladium oxide on charcoal (50% aq. paste, 0.2 g) for 4 h until hydrogen uptake ceased (240 ml). The catalyst was filtered off, and the filtrate evaporated in vacuo to give an oil which was crystallised from ethyl acetate to give the title compound as a solid (1.8 g) m.p. 122°-124°.

T.l.c. (R) Rf 0.4 (Ce^{IV}).

(iii) N,N-Dimethyl-5-[2-[(methylamino)sulphonyl]ethyl]-αoxo-1H-indole-3-acetamide Oxalyl chloride (0.3 ml) was added dropwise, under nitrogen, to a stirred solution of the product of Stage (ii) (0.7 g) in tetrahydrofuran (30 ml) and the resulting solution stirred at room temperature for 1 h. Dimethylamine gas was then bubbled through the solution for 10 min. The resulting suspension was partitioned between hydrochloric acid (2N, 50 ml) and ethyl acetate (2×50 ml). The combined extracts were dried (Na₂SO₄) and evaporated in vacuo to give an oil which was purified by 'flash' chromatography (S, 4 cm dia. col). The resulting oil was crystallised from a mixture of ethyl acetate and hexane to give the title compound as a solid (0.4 g) m.p. 151°-153°.

(iv) 3-[2-(Dimethylamino)ethyl]-N-methyl-1H-indole-5-ethanesulphonamide hydrochloride hemihydrate A solution of the product of Stage (iii) (0.3 g) in tetrahydrofuran (30 ml) containing lithium aluminium hydride (0.3 g) was heated at reflux for 3 h, cooled, and excess reducing agent decomposed by addition of 10% aq. THF. The resulting mixture was partitioned between sodium carbonate (2N, 100 ml) and ethyl acetate (2×50 ml). The combined extracts were dried (Na₂SO₄) and evaporated in vacuo to give an oil which was purified by 'flash' chromatography (A, 4 cm dia. col.). The resulting oil (0.15 g) was dissolved in absolute ethanol (5 ml), acidified with ethereal hydrogen chloride and the salt precipitated by adding excess dry ether. The salt was filtered off, and dried in vacuo to give the title compound as a solid (0.12 g) m.p. 86°-92° C. (softens at 62° C.) which was shown by n.m.r. and t.l.c. (A, Rf 0.4) to be identical with the product of Method (I).

Method (VI)

A solution of the product of Example 1 as the free base (0.4 g) in n-propanol (16 ml), chilled in an ice-bath was treated with aqueous formaldehyde (~40% soln, 0.64 ml) and the resultant suspension stirred for 0.75 h, under an atmosphere of nitrogen. Sodium borohydride (0.54 g) was added and the resulting mixture stirred in an ice-bath for 2 h. The suspension was treated with 2N hydrochloric acid (~6 ml), and stirred for 10 min. The resulting mixture was evaporated to low volume (keeping the temperature below (50°) basified with 8% aq. sodium bicarbonate solution (20 ml) and extracted with ethyl acetate (5×15 ml). The combined extracts were dried (MgSO₄) and evaporated to produce an oil (0.35 g) which was chromatographed (B) to give the tryptamine as an oil (0.148 g). Part of the oil (0.140 g) in absolute ethanol (2 ml) was treated with excess ethereal HCl (4 ml) and evaporated to dryness to leave a semisolid which was triturated with anhydrous ether to present the title compound as a solid (0.1 g) m.p. 130-136 (softens at 128°) which was shown by n.m.r and t.l.c. (A, Rf 0.3) to be identical with the product of Method (I).

Method (VII)

To a solution of the product of Example 12 (146 mg) in anhydrous tetrahydrofuran (15 ml) at ambient temperature was added tetrabutylammonium fluoride (0.99 ml 1.0M solution in THF). After stirring at ambient temperature for a period of 40 min, propylene oxide (100 μl) was added followed by methyl iodide (1 ml of 0.25M soln. in THF) and the mixture kept for 40 min at ambient temperature, then quenched with aqueous sodium thiosulphate solution (20 ml, 10% solution) and extracted with ethyl acetate (2×15 ml). The organic extracts were dried (Na₂SO₄) and concentrated in vacuo. T.l.c. examination (D) of the reaction mixture indicated the presence of the title compound (Rf 0.50) which was identical with a sample prepared by Method (I).

EXAMPLE 11

3-[2-(Dimethylamino)ethyl]-N-methyl-1H-indole-5-ethanesulphonamide oxalate

A hot solution of the product of Example 10 as the free base (0.13 g) was treated with oxalic acid (40 mg) in ethanol (2 ml) and the oxalate salt precipitated at once. Solvent was evaporated and the residual solid crystallised from hot methanol (10 ml) to give the title compound as a solid (80 mg) m.p. 198°-199°.

Analysis Found: C,50.9;H,6.2;N,10.4.
C₁₅H₂₃N₃O₂S.C₂H₂O₄ requires C,51.1;H,6.3;N,10.5%.

T.l.c. (L) Rf 0.2 (IPA, Ce).

EXAMPLE 12

3-[2-(Dimethylamino)ethyl]-1H-indole-5-ethanesulphonamide oxalate

A mixture of the product of Example 18 stage (v) (70 mg) in liquid ammonia (15 ml) was heated in an autoclave at 110° C. for 3 h and then at 175° C. for an additional 2 h. On cooling to ambient temperature, ammonia was allowed to evaporate off and the autoclave recharged with pyridine (2 ml) and liquid ammonia (15 ml). After 14 h at 155° C., the autoclave was cooled to ambient temperature and ammonia left to evaporate. The mixture was concentrated in vacuo and the resulting gum purified by flash chromatography to afford the product as a glass, (15.3 mg) which was taken up in ethanol (0.25 ml), filtered and added to a solution of oxalic acid (4.6 mg) in ethanol (0.5 ml). On concentrating in vacuo, a solid deposited, which was filtered, washed with ether and dried in vacuo overnight to afford the title compound, (5 mg).

T.l.c. (A) Rf 0.23 (IPA,KMnO₄).

N.m.r. δ(CD₃SOCD₃)2.83 (6H,s,NMe₂), 3.0-3.4(8H,m,CH₂CH₂—NMe₂ and CH₂CH₂SO₂), 6.92(2H,br,SO₂NH₂), 7.0-7.6(4H,m,aromatic).

EXAMPLE 13

3-[2-(Dimethylamino)ethyl]-1H-indole-5-ethanesulphonamide (i)

(E)-2-[3-(Cyanomethyl)-1H-indol-5-yl]ethenesulphonamide

A solution of ethenesulphonamide (428 mg), 5-bromo-3-(cyanomethyl)-1H-indole (940 mg), palladium II acetate (21 mg) tri-o-tolylphosphine (67 mg) and dry triethylamine (1.1 ml) in dry acetonitrile (15 ml) was heated in an autoclave at 130° C. for 48 h. On cooling to ambient temperature, the mixture was poured into water (30 ml) and extracted with ethyl acetate 3×30 ml). The combined organic extracts were dried (MgSO4) and concentrated in vacuo. Flash chromatography (B) of the residue afforded a powder. Recrystallization (hexane-dichloromethane) afforded the title compound as a powder (550 mg) m.p. 176°-178°.

(ii) 3-(Cyanomethyl)-1H-indole-5-ethanesulphonamide

A solution of the product of stage (i) (443.6 mg) in absolute ethanol (50 ml) was hydrogenated at room temperature and pressure over pre-reduced 10% palladium oxide on charcoal (1.30 g, 50% aqueous paste in absolute ethanol, 30 ml) for a period of 18 h. The catalyst was removed by filtration through a sand-celite pad, which was then washed well with ethanol (200 ml). The combined filtrates were concentrated in vacuo and the residue purified by flash (B) chromatography to afford a viscous oil, which solidified on trituration with diethyl ether to afford the title compound as an amorphous powder. (260 mg) m.p. 109°-111°.

(iii) 3-[2-1H-indole-5-ethanesulphonamide

A solution of the product of stage (ii) (4.9 mg) in ethanolic dimethylamine (33%, 5 ml) was hydrogenated at room temperature and pressure over pre-reduced 10% palladium oxide on charcoal (10 mg, 50% aqueous paste, pre-reduced in absolute ethanol, 5 ml) for 14 h. The mixture was filtered through a sand-celite pad, which was then washed with further quantities of ethanol (3×10 ml), and the combined filtrates concentrated in vacuo. Flash chromatography (A) of the residue afforded the title compound (3.7 mg) which was shown by t.l.c. (A. Rf 0.22) and n.m.r. to be identical with the product of Example 12.

EXAMPLE 14

3-[2-(Ethylmethylamino)ethyl]-N-methyl-1H-indole-5-ethanesulphonamide hydrochloride (i)

N-Ethylmethyl-5-[2-[(methylamino)sulphonyl]ethyl]-1H-indole-3-acetamide

A solution of the product of Example 10 (II) stage (i) (0.7 g) in dry tetrahydrofuran (THF) (50 ml) containing carbonyldiimidazole (0.5 g) was stirred at room temperature for 1 h. N-Methylethylamine (2 ml) was added, and the solution stirred at room temperature for 3 h. The solution was partitioned between 2N hydrochloric acid (50 ml) and ethyl acetate (2×50 ml). The combined extracts were washed with 2N sodium carbonate (50 ml), dried (Na2SO4) and evaporated in vacuo to give an oil. The oil was purified by 'flash' chromatography eluting with ethyl acetate to give the title compound as an oil (0.2 g).

T.l.c. ethyl acetate (Ce$^{IV}$) Rf 0.2.

(ii)

3-[2-(Ethylmethylamino)ethyl]-N-methyl-1H-indole-5-ethanesulphonamide hydrochloride A solution of the product of stage (i) (0.2 g) in dry THF (50 ml) containing lithium aluminum hydride (0.2 g) was heated at reflux for 24 h, cooled, and excess reducing agent decomposed by addition of 10% aq. THF. The resulting mixture was partitioned between 2N sodium carbonate (50 ml) and ethyl acetate (2×50 ml). The combined extracts were dried (Na2SO4) and evaporated in vacuo to give an oil, which was dissolved in ethanol (5 ml), acidified with ethereal hydrogen chloride and the salt precipitated by adding excess dry ether (300 ml). The salt was filtered off and dried in vacuo to give the title compound as a hygroscopic solid. (0.08 g) m.p. 95°-99° C.

Analysis Found: C,53.0;H,7.6;N,11.4.
C16H25N3O2S.HCl requires C,53.4;H,7.3;N,11.7%.
N.m.r. δ(CD3SOCD3)1.28(3H,t,CH2CH3),2.65(3H,d,SO2NHCH3),2.81(3H,s,CH2NCH3),3.0-3.5(m,CH2CH2SO2 and CH2CH2NMe and NCH2CH3),7.0-7.6(5H,m, aromatics+SO2NH).

EXAMPLE 15

N-Methyl-3-[2-(2-propenylamino)ethyl]-1H-indole-5-ethanesulphonamide oxylate hydrate (i)

5[2-[(Methylamino)sulphonyl]ethyl]-N-(2-propenyl)-1H-indole-3-acetamide

A solution of the product of Example 10 (II) stage (i) (0.7 g) in dry tetrahydrofuran (THF) (50 ml) containing carbonyldiimidazole (0.5 g) was stirred at room temperature for 1 h. Allylamine (2 ml) was added, and the solution stirred at room temperature for 3 h. The solution was partitioned between 2N hydrochloric acid (50 ml) and ethyl acetate (2×50 ml). The combined extracts were dried (Na2SO4) and evaporated in vacuo to give an oil. The oil was purified by 'flash' chromatography eluting with ethyl acetate to give the title compound as an oil (0.25 g) which crystallised on standing. m.p. 123°-125° C.

(ii)

N-Methyl-3-[2-(2-propenylamino)ethyl]-1H-indole-5-ethanesulphonamide oxalate

A solution of the product of stage (i) (0.2 g) in dry THF (50 ml) containing lithium aluminum hydride (0.4 g) was heated at reflux for 24 h, cooled, and excess reducing agent destroyed by adding 10% aq. THF. The resulting mixture was partitioned between 5N hydrochloric acid (50 ml) and ethyl acetate (30 ml). The aqueous layer was basified (Na2CO3) and extracted with ethyl acetate (2×50 ml). The combined extracts were dried (Na2SO4) and evaporated in vacuo to give an oil (82 mg), which was dissolved in ethanol (5 ml), acidified with a solution of oxalic acid (25 mg) in methanol (2 ml) and the solution evaporated in vacuo. Trituration with dry ether gave the title compound as a solid. (80 mg) m.p. 105°-108° C.

Analysis Found: C,49.7;H,6.2;N,9.6.
C16H23N3O2S.C2H2O4.1.5 H2O requires C,49.3;H,6.4;N,9.6%.
N.m.r. (free base) δ(CD3SOCD3)2.65(3H,s,SO2NH-Me),3.0-3.4(10H,m, CH2CH2SO2 and CH2CH2N and NCH$_2$CH=), 5.17(2H,m,—CH=CH$_2$), 5.88(1H,m, —CH=CH$_2$), 7.0–7.5(4H, m,aromatic).

EXAMPLE 16

N-Methyl-3-[2-[(phenylmethylidene)amino]ethyl]-1H-indole-5-ethanesulphonamide A solution of the free base of the product from Example 1 (1.0 g) in absolute ethanol (10 ml) containing freshly distilled benzaldehyde (0.04 g) and 3Å molecular sieves (0.5 g) was stirred under nitrogen at reflux for 2 h and then at room temperature for 48 h. The suspension was filtered through "hyflo" and the filtrate evaporated under reduced pressure to produce a gum (0.036 g). Trituration with anhydrous ether presented the title compound as a powder (0.01 g) m.p. 146°–148°.

N.m.r. $\delta$(CD$_3$SOCD$_3$/CDCl$_3$)2.72(3H,d,SO$_2$NH-Me)3.08–3.32(6H,m,CH$_2$CH$_2$SO$_2$ and CH$_2$CH$_2$N=), 6.3(1H,brq,SO$_2$NH)7.38–7.7(6H,m,N=CH—Ph and indole-4)8.18(1H,s,N=CH).

EXAMPLE 17

3-[2-(Dimethylamino)ethyl]-N-(2-propenyl)-1H-indol-5-ethanesulphonamide

A solution of the product of Example 18 stage (v) (30 mg) and allylamine (2 ml) in dry pyridine was heated to 100° in a "reactival" for 36 h. The cooled reaction mixture was concentrated in vacuo and purified by 'flash' chromatography (A) to afford the title compound as a viscous oil (3.4 mg).

T.l.c. (A) Rf 0.36 (IPA).

N.m.r. $\delta$(CD$_3$SOCD$_3$)2.26(6H,s,NMe$_2$) 3.68(2H,brt,CH$_2$CH=CH$_2$)5.17(1H,dd,CH=CH$_2$, C-proton),5.32(1H,dd,CH=CH$_2$, z-proton)5.9(1H,ddl,CH=CH$_2$), 7.4(2H,br,SO$_2$NH and indole-4).

EXAMPLE 18

3-[2-(Dimethylamino)ethyl]-N-methyl-1H-indole-5-ethanesulphonamide

(i) Phenyl 4-nitrobenzeneethanesulphonate

To a solution of 4-nitrobenzeneethanesulphonyl chloride (14.4 g) in benzene (200 ml) and tetrahydrofuran (THF) (5 ml) was added phenol (5.5 g) and triethylamine (8.5 ml) in THF (20 ml) with ice cooling and the resulting suspension was stirred at room temperature for 1 h. The resulting mixture was washed with dilute hydrochloric acid (2×20 ml), dried (MgSO$_4$) and concentrated to an oil, which solidified on standing. The solid was washed with ether (400 ml) and air-dried for 1 h to give the phenylsulphonate (11.45 g). A sample (400 mg) was recrystallized from ethanol (20 ml) to give the title compound as a solid (250 mg) m.p. 90°–91°.

(ii) Phenyl 4-aminobenzeneethanesulphonate hydrochloride

To pre-reduced 10% palladium oxide (2 g; as 50% paste with water) in ethanol (50 ml) was added a suspension of the product of stage (i) (11 g) in ethanol (100 ml) and ethyl acetate (200 ml) which was hydrogenated at atmospheric pressure and temperature for 2 h. Hydrogen uptake was 1.91. The catalyst was filtered off (Hyflo), washed with more ethanol (250 ml), the solvent evaporated and the residual oil dissolved in chloroform (200 ml). Ethanolic hydrogen chloride was added to the solution (to pH1) and the title compound precipitated as a solid (3.1 g).

T.l.c. methylene chloride Rf 0.25 (Ce$^{II}$).

(iii) Phenyl 4-hydroazinobenzeneethanesulphonate hydrochloride

To a suspension of the product of stage (ii) (1 g) in conc. hydrochloric acid (10 ml) and water (10 ml) was added sodium nitrite (0.46 g) in water (2 ml) at −5° (ice-salt bath). More water was added (20 ml), the resulting suspension filtered and the filtrate added to a solution of stannous chloride (6.6 g) in conc. hydrochloric acid (10 ml) at −5°. The mixture was stirred at room temperature for 16 h. The resulting solid was filtered off, washed with ether (50 ml) and air-dried for 30 min. to give the title compound (0.51 g) contaminated with inorganic material. This was used in the next step without further purification.

T.l.c. (A) Rf 0.75.

(iv) Phenyl 4-[2-[4-(dimethylamino)butylidene]hydrazino]benzene ethanesulphonate A suspension of the product of stage (iii) (0.5 g) and 4,4-dimethoxy-N,N-dimethylbutanamine (0.5 g) in water (10 ml) and dilute hydrochloric acid (2N; 5 ml; pH 1) was stirred at room temperature for 2 h. The resulting solution was saturated with potassium carbonate and extracted with ethyl acetate (4×20 ml). The extract was dried and evaporated to give the title compound as an oil (0.33 g) which was used in the next step without further purification.

T.l.c. (A) Rf 0.5 (CeIV, IPA).

(v) Phenyl 3-[2-(dimethylamino)ethyl]-1H-indole-5-ethanesulphonate

The product of stage (iv) (0.33 g) in polyphosphate ester (3.3 g) and chloroform (8 ml) was heated at reflux for 10 min, poured onto ice (20 mg) and neutralised with solid potassium carbonate. The aqueous layer was extracted with chloroform (4×15 ml), the extracts combined, washed with brine (2×10 ml), dried and evaporated. The residue was chromatographed (B) to give the slightly impure product as an oil (0.1 g). A small sample (15 mg) was re-purified by preparative layer chromatography (L, 20×20 cm; 2 mm) to give the pure title compound as an oil (7 mg)

T.l.c (A) Rf 0.5 (CeIV, IPA).

(vi) 3-[2-(Dimethylamino)ethyl]-N-methyl-1H-indole-5-ethanesulphonamide

The product of stage (v) (70 mg) in a saturated solution of methylamine in pyridine (4 ml) was heated at 100° in a "reactival" for 1.5 h. The mixture was concentrated and the residue oil purified by column chromatography (B) to give the title compound as an oil (7 mg), which was shown by n.m.r. and t.l.c. (B, Rf 0.3) to be identical with the product of Example 10 method (I).

The following examples illustrate pharmaceutical formulations according to the invention, containing 3-[2-(dimethylamino)ethyl]-N-methyl-1H-indole-5-ethanesulphonamide hydrochloride as the active ingredient. Other compounds of the invention may be formulated in a very similar manner.

TABLETS FOR ORAL ADMINISTRATION

These may be prepared by conventional methods such as direct compression or wet granulation.

| A DIRECT COMPRESSION | | |
| --- | --- | --- |
|  | mg/tablet | For 20 g Mix |
| Active ingredient | 2.24 | 0.448 g |
| Calcium hydrogen phosphate R.P.* | 95.26 | 19.052 g |
| Croscarmellose sodium USP | 2.00 | 0.400 g |
| Magnesium stearate, B.P. | 0.50 | 0.100 g |
| Compression weight | 100 mg | |

*of a grade suitable for direct compression

The active ingredient was sieved before use. The calcium hydrogen phosphate, croscarmellose sodium and active ingredient were weighed into a clean polythene bag. The powders were mixed by vigorous shaking for 5 minutes. The magnesium stearate was weighed, added to the mix which was blended for a further 2 minutes. The mix was then compressed using a Manesty F3 tablet machine fitted with 5.5 mm flat bevelled edge punches, into tablets with target fill weight of 100 mg.

| B WET GRANULATION | |
| --- | --- |
|  | mg/tablet |
| Active ingredient | 2.24 |
| Lactose BP | 151.5 |
| Starch BP | 30.0 |
| Pregelatinised Maize Starch BP | 15.0 |
| Magnesium Stearate BP | 1.5 |
| Compression weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

| CAPSULES | |
| --- | --- |
|  | mg/capsule |
| Active ingredient | 28.00 |
| Starch 1500 | 174.00 |
| Magnesium Stearate BP | 1.00 |
| Fill Weight | 200.00 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

| SYRUP | |
| --- | --- |
|  | mg/5 ml dose |
| Active ingredient | 28.00 |
| Buffer | |
| Flavour | |
| Colour | |

| -continued SYRUP | | |
| --- | --- | --- |
|  |  | mg/5 ml dose |
| Preservative | | |
| Thickening agent | | |
| Sweetening agent | | |
| Purified Water | to | 5.00 ml |

The active ingredient, buffer, flavour, colour, preservative, thickening agent and sweetening agent are dissolved in some water, the solution is adjusted to volume and mixed. The syrup produced is classified by filtration.

| SUSPENSION | | |
| --- | --- | --- |
|  |  | mg/5 ml dose |
| Active ingredient | | 28.00 |
| Aluminium monostearate | | 75.00 |
| Sweetening agent | | |
| Flavour | | as required |
| Colour | | |
| Fractionated coconut oil | to | 5.00 ml |

The aluminum monostearate is dispersed in about 90% of the fractionated coconut oil. The resulting suspension is heated to 115° C. while stirring and then cooled. The sweetening agent, flavour and colour are added and the active ingredient is suitably dispersed. The suspension is made up to volume with the remaining fractionated coconut oil and mixed.

| TABLET FOR BUCCAL ADMINISTRATION | |
| --- | --- |
|  | mg/tablet |
| Active ingredient | 2.24 |
| Lactose BP | 94.56 |
| Sucrose BP | 86.7 |
| Hydroxypropylmethylcellulose | 15.0 |
| Magnesium Stearate BP | 1.5 |
| Compression weight | 200.00 |

The active ingredient is sieved through a suitable sieve and blended with the lactose, sucrose and hydroxypropylmethylcellulose. Suitable volumes of purified water are added and the powders are granulated. After drying, the granules are then compressed into tablets using suitable punches.

| SUPPOSITORY FOR RECTAL ADMINISTRATION | | |
| --- | --- | --- |
| Active ingredient |  | 5.6 mg |
| *Witepsol H15 | to | 1.0 g |

*A proprietary grade of Adeps Solidus Ph. Eur.

A suspension of the active ingredient in molten Witepsol is prepared and filled, using suitable machinery, into 1 g size suppository moulds.

| INJECTION FOR INTRAVENOUS ADMINISTRATION | | |
| --- | --- | --- |
|  |  | mg/ml |
| Active ingredient |  | 1.12 mg |
| Sodium Chloride BP |  | as required |
| Water for Injection BP | to | 1.0 ml |

Sodium chloride may be added to adjust the tonicity of the solution and the pH may be adjusted, using acid or alkali, to that of optimum stability and/or to facilitate solution of the active ingredient. Alternatively suitable buffer salts may be used.

The solution is prepared, classified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

| FOR INHALATION INHALATION CARTRIDGES | | |
|---|---|---|
| | | mg/cartridge |
| Active ingredient (micronised) | | 16.8 |
| Lactose BP | to | 25.00 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler.

| METERED DOSE PRESSURISED AEROSOL | | |
|---|---|---|
| | mg/metered dose | per can |
| Active ingredient (micronised) | 0.560 | 134.4 mg |
| Oleic Acid BP | 0.050 | 12 mg |
| Trichlorofluoromethane BP | 22.25 | 5.34 g |
| Dichlorodifluoromethane BP | 60.90 | 14.62 g |

The active ingredient is micronised in a fluid energy mill to a fine particle size range. The oleic acid is mixed with the trichlorofluoromethane at a temperature of 10°-15° C. and the micronised drug is mixed into this solution with a high shear mixer. The suspension is metered into aluminum aerosol cans and suitable metering valves, delivering a metered dose of 85 mg of suspension, are crimped onto the cans and the dichlorodifluoromethane is pressure filled into the cans through the valves.

We claim:

1. A compound having a formula as follows:

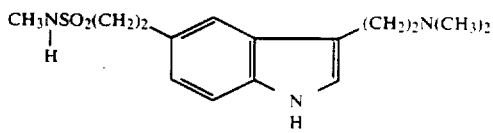

or a physiologically acceptable salt or solvate thereof.

2. A process for the treatment of pain resulting from dilatation of the cranial vasculature which comprises administering to a patient an effective amount of a compound as claimed in claim 1 to relieve said pain.

3. A physiologically acceptable salt of a compound according to claim 1 which is selected from the hydrochloride, hydrobromide, sulphate, fumarate, maleate and succinate.

4. A pharmaceutical composition which comprises at least one compound of formula (I) of claim 1 or a physiologically acceptable salt or solvate thereof together with a physiologically acceptable carrier therefor.

5. A pharmaceutical composition according to claim 4 which is formulated for oral administration.

* * * * *